(12) United States Patent
Popplewell et al.

(10) Patent No.: US 7,355,011 B2
(45) Date of Patent: Apr. 8, 2008

(54) BIOLOGICAL PRODUCTS

(75) Inventors: Andrew George Popplewell, Slough (GB); Simon Peter Tickle, Slough (GB); Heather Margaret Ladyman, Slough (GB)

(73) Assignee: UCB Pharma S.A., Brussels (BE)

( * ) Notice: Subject to any disclaimer, the term of this patent is extended or adjusted under 35 U.S.C. 154(b) by 593 days.

(21) Appl. No.: 10/428,408

(22) Filed: May 2, 2003

(65) Prior Publication Data

US 2003/0235869 A1    Dec. 25, 2003

(30) Foreign Application Priority Data

May 2, 2002    (GB)    .................................. 0210121.0

(51) Int. Cl.
*C07K 16/00*    (2006.01)

(52) U.S. Cl. ................ 530/387.3; 530/387.1; 530/387.7; 530/388.1; 435/7.1; 424/130.1; 424/184.1; 424/277.1

(58) Field of Classification Search ............. 536/23.53; 424/130.1, 133.1, 145.1, 387.1, 387.3, 388.23, 424/184.1, 277.1; 530/387.3, 387.1, 387.7, 530/388.1; 435/7.1
See application file for complete search history.

(56) References Cited

U.S. PATENT DOCUMENTS 5,686,072 A    11/1997    Uhr et al.
5,693,762 A *  12/1997    Queen et al. ............. 530/387.3

FOREIGN PATENT DOCUMENTS

| EP | 0 239 400 A2 | 9/1987 |
|---|---|---|
| RU | 97104205 A | 5/1999 |
| RU | 2131423 C1 | 6/1999 |
| WO | WO 90/07861 | 7/1990 |
| WO | WO 91/09967 | 7/1991 |
| WO | WO 96/04925 | 2/1996 |
| WO | WO 98/41641 | 9/1998 |
| WO | WO 98/42378 | 10/1998 |

OTHER PUBLICATIONS

Paul, Fundamental Immunology, 3rd ed, (textbook), pp. 292-295, 1993.*
Rudikoff et al (Proc. Natl. Acad. Sci. USA, (79):1979-1983, 1982.*
Vose (Cytotherapy, 2000. 2(6):455-461).*
Riechmann, Lutz et al.,"Reshaping Human Antibodies for Therapy," *Nature*, 332:323-327, Mar. 1988.
Verhoeyen, Martine et al., "Reshaping Human Antibodies: Grafting an Antilysozyme Activity," *Science*, 239:1534-1536, Mar. 1988.

* cited by examiner

*Primary Examiner*—David J. Blanchard
*Assistant Examiner*—Parithosh K. Tungaturthi
(74) *Attorney, Agent, or Firm*—Cozen O'Connor

(57) ABSTRACT

There is disclosed antibody molecules containing at least one CDR derived from a mouse monoclonal antibody having specificity for human CD22. There is also disclosed a CDR grafted antibody wherein at least one of the CDRs is a modified CDR. Further disclosed are DNA sequences encoding the chains of the antibody molecules, vectors, transformed host cells and uses of the antibody molecules in the treatment of diseases mediated by cells expressing CD22.

5 Claims, 19 Drawing Sheets

Figure 1:     Sequence of CDRs of mouse monoclonal 5/44

H1  NYWIH              (SEQ ID NO:1)

H2  GINPGNNYTTYKRNLKG  (SEQ ID NO:2)

H3  EGYGNYGAWFAY       (SEQ ID NO:3)

L1  RSSQSLANSYGNTFLS   (SEQ ID NO:4)

L2  GISNRFS            (SEQ ID NO:5)

L3  LQGTHQPYT          (SEQ ID NO:6)

Figure 2:    DNA/Protein sequence of 5/44 V$_L$

```
            10          20          30          40          50
   GAT GTT GTG GTG ACT CAA ACT CCA CTC TCC CTG CCT GTC AGC TTT GGA GAT CAA GTT
   CTA CAA CAC CAC TGA GTT TGA GGT GAG AGG GAC GGA CAG TCG AAA CCT CTA GTT CAA
    D   V   V   V   T   Q   T   P   L   S   L   P   V   S   F   G   D   Q   V>

60          70          80          90         100         110
   TCT ATC TCT TGC AGG TCT AGT CAG AGT CTT GCA AAC AGT TAT GGG AAC ACC TTT TTG
   AGA TAG AGA ACG TCC AGA TCA GTC TCA GAA CGT TTG TCA ATA CCC TTG TGG AAA AAC
    S   I   S   C   R   S   S   Q   S   L   A   N   S   Y   G   N   T   F   L>

120         130         140         150         160         170
   TCT TGG TAC CTG CAC AAG CCT GGC CAG TCT CCA CAG CTC CTC ATC TAT GGG ATT TCC
   AGA ACC ATG GAC GTG TTC GGA CCG GTC AGA GGT GTC GAG GAG TAG ATA CCC TAA AGG
    S   W   Y   L   H   K   P   G   Q   S   P   Q   L   L   I   Y   G   I   S>

180         190         200         210         220
   AAC AGA TTT TCT GGG GTG CCA GAC AGG TTC ACT GGC AGT GGT TCA GGG ACA GAT TTC
   TTG TCT AAA AGA CCC CAC GGT CTG TCC AAG TGA CCG TCA CCA AGT CCC TGT CTA AAG
    N   R   F   S   G   V   P   D   R   F   T   G   S   G   S   G   T   D   F>

230         240         250         260         270         280
   ACA CTC AAG ATC AGC ACA ATA AAG CCT GAG GAC TTG GGA ATG TAT TAC TGC TTA CAA
   TGT GAG TTC TAG TCG TGT TAT TTC GGA CTC CTG AAC CCT TAC ATA ATG ACG AAT GTT
    T   L   K   I   S   T   I   K   P   E   D   L   G   M   Y   Y   C   L   Q>

290         300         310         320         330
   GGT ACA CAT CAG CCG TAC ACG TTC GGA GGG GGG ACC AAG CTG GAA ATA AAA CGT
   CCA TGT GTA GTC GGC ATG TGC AAG CCT CCC CCC TGG TTC GAC CTT TAT TTT GCA
    G   T   H   Q   P   Y   T   F   G   G   G   T   K   L   E   I   K   R>
```

Figure 3: DNA/Protein sequence of 5/44 V$_H$

```
             10          20          30          40          50
     GAG GTC CAA CTG CAG CAG TCT GGG ACT GTA CTG GCA AGG CCT GGG GCT TCC GTG AAG
     CTC CAG GTT GAC GTC GTC AGA CCC TGA CAT GAC CGT TCC GGA CCC CGA AGG CAC TTC
      E   V   Q   L   Q   Q   S   G   T   V   L   A   R   P   G   A   S   V   K>

60          70          80          90         100         110
     ATG TCC TGC AAG GCT TCT GGC TAC AGG TTT ACC AAC TAC TGG ATT CAC TGG GTA AAA
     TAC AGG ACG TTC CGA AGA CCG ATG TCC AAA TGG TTG ATG ACC TAA GTG ACC CAT TTT
      M   S   C   K   A   S   G   Y   R   F   T   N   Y   W   I   H   W   V   K>

120         130         140         150         160         170
     CAG AGG CCT GGG CAG GGT CTA GAA TGG ATT GGT GGT ATT AAT CCT GGA AAT AAT TAT
     GTC TCC GGA CCC GTC CCA GAT CTT ACC TAA CCA CCA TAA TTA GGA CCT TTA TTA ATA
      Q   R   P   G   Q   G   L   E   W   I   G   G   I   N   P   G   N   N   Y>

180         190         200         210         220
     ACT ACG TAT AAG AGG AAC TTG AAG GGC AAG GCC ACA CTG ACT GCA GTC ACA TCC GCC
     TGA TGC ATA TTC TCC TTG AAC TTC CCG TTC CGG TGT GAC TGA CGT CAG TGT AGG CGG
      T   T   Y   K   R   N   L   K   G   K   A   T   L   T   A   V   T   S   A>

230         240         250         260         270         280
     AGC ACT GCC TAC ATG GAC CTC AGC AGC CTG ACA AGT GAG GAC TCT GCG GTC TAT TAC
     TCG TGA CGG ATG TAC CTG GAG TCG TCG GAC TGT TCA CTC CTG AGA CGC CAG ATA ATG
      S   T   A   Y   M   D   L   S   S   L   T   S   E   D   S   A   V   Y   Y>

290         300         310         320         330         340
     TGT ACA AGA GAG GGC TAT GGT AAC TAC GGG GCC TGG TTT GCT TAC TGG GGC CAG GGG
     ACA TGT TCT CTC CCG ATA CCA TTG ATG CCC CGG ACC AAA CGA ATG ACC CCG GTC CCC
      C   T   R   E   G   Y   G   N   Y   G   A   W   F   A   Y   W   G   Q   G>

350         360
     ACT CTG GTC ACC GTC TCC TCA
     TGA GAC CAG TGG CAG AGG AGT
      T   L   V   T   V   S   S>
```

Figure 4: Removal of Glycosylation Site and Reactive Lysine
PCR strategy to mutate CDR-H2 in cH vector
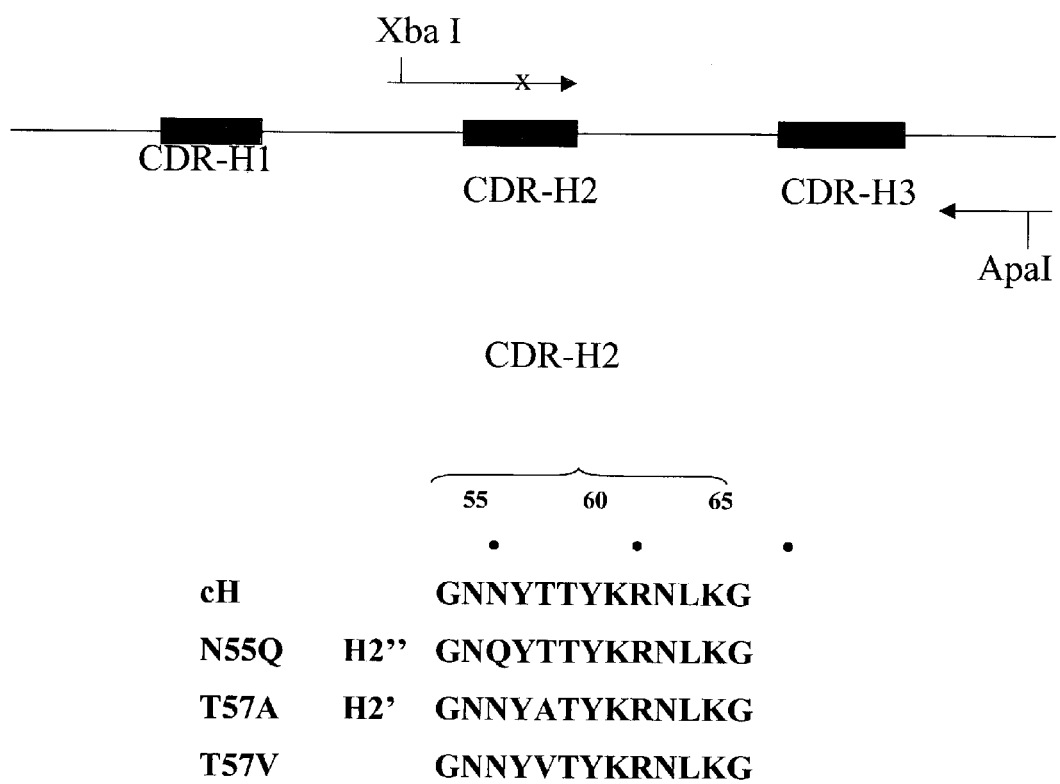

Figure 5:    5/44 Light Chain Sequence Graft design

```
             10        20                            40
V_L   DVVVTQTPLSLPVSFGDQVSISC   RSSQSLANSYGNTFLS   WYLHKPGQSPQLLIY
      ||| | || | |||                              ||    || |
DPK9  DIQMTQSPSSLSASVGDRVTITC                      WYQQKPGKAPKLLIY
      | |                                          ||     |
gL1   DVQVTQSPSSLSASVGDRVTITC   RSSQSLANSYGNTFLS   WYLHKPGKAPQLLIY
gL2   DVVVTQSPSSLSASVGDRVTITC   RSSQSLANSYGNTFLS   WYLHKPGKAPQLLIY 60        70        80        90
V_L   GISNRFS  GVPDRFTGSGSGTDFTLKISTIKPEDLGMYYC   LQGTHQPYT
               | |           |  |||   |||
DPK9           GVPSRFSGSGSGTDFTLTISSLQPEDFATYYC
                              |
gL1   GISNRFS  GVPDRFSGSGSGTDFTLTISSLQPEDFATYYC   LQGTHQPYT
gL2   GISNRFS  GVPDRFSGSGSGTDFTLTISSLQPEDFATYYC   LQGTHQPYT

100
V_L   FGGGTKLEIKR
           |  |
JK1   FGQGTKVEIKR gL1   FGQGTKVEIKR
gL2   FGQGTKVEIKR
```

DPK-9 is the human germ-line acceptor framework sequence.

Vertical lines indicate differences between mouse and human residues.

Sequences underlined indicate donor residues which have been retained in the graft.
CDRs are indicated in blue (not shown for DPK-9).

Graft gL1 has 6 donor framework residues, gL2 has 7.

Figure 6: 5/44 Heavy Chain Sequence Graft design

```
                  10          20          30          40          50
V_H      EVQLQQSGTVLARPGASVKMSCKASGYRFT  NYWIH  WVKQRPGQGLEWIG  GINP
           |    | |||||       |                  | |            |
DP7      QVQLVQSGAEVKKPGASVKVSCKASGYTFT         WVRQAPGQGLEWMG
           |                  |                        |
gH1      EVQLVQSGAEVKKPGASVKVSCKASGYRFT  NYWIH  WVRQAPGQGLEWIG  GINP
gH4,5,6,7 EVQLVQSGAEVKKPGASVKVSCKASGYRFT  NYWIH  WVRQAPGQGLEWIG  GINP 60          70          80          90          100
V_H      GNNYTTYKRNLKG  KATLTAVTSASTAYMDLSSLTSEDSAVYYCTR  EGYGNYG
            || | ||    |  | |    |    |    |       |
DP7              KFQG  RVTMTRDTSTSTVYMELSSLRSEDTAVYYCAR
                       | | |                           |
gH1      GNQYTTYKRNLKG  RATLTADTSTSTVYMELSSLRSEDTAVYYCTR  EGYGNYG
gH4      GNNYATYRRNLKG  RATLTADTSTSTVYMELSSLRSEDTAVYYCTR  EGYGNYG
gH5      GNNYATYRRNLKG  RVTMTADTSTSTVYMELSSLRSEDTAVYYCTR  EGYGNYG
gH6      GNNYATYRRKFQG  RATLTADTSTSTVYMELSSLRSEDTAVYYCTR  EGYGNYG
gH7      GNNYATYRRKFQG  RVTMTADTSTSTVYMELSSLRSEDTAVYYCTR  EGYGNYG

110
JH4              WGQGTLVTVSS

V_H       AWFAY  WGQGTLVTVSS
gH1       AWFAY  WGQGTLVTVSS
gH4,5,6,7 AWFAY  WGQGTLVTVSS
```

DP7 is the human germ-line acceptor framework sequence.

Vertical lines indicate differences between mouse and human residues.

Sequences underlined indicate donor residues which have been retained in the graft. CDRs are indicated in blue (not shown for DP7)

Grafts gH4 and gH6 have 6 donor framework residues. Grafts gH5 and gH7 have 4.

Figure 7: Maps of pMRR14 and pMRR10.1
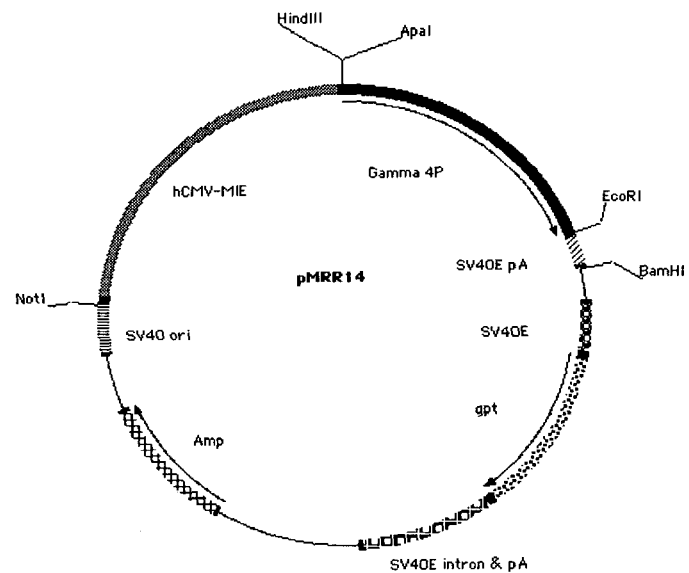
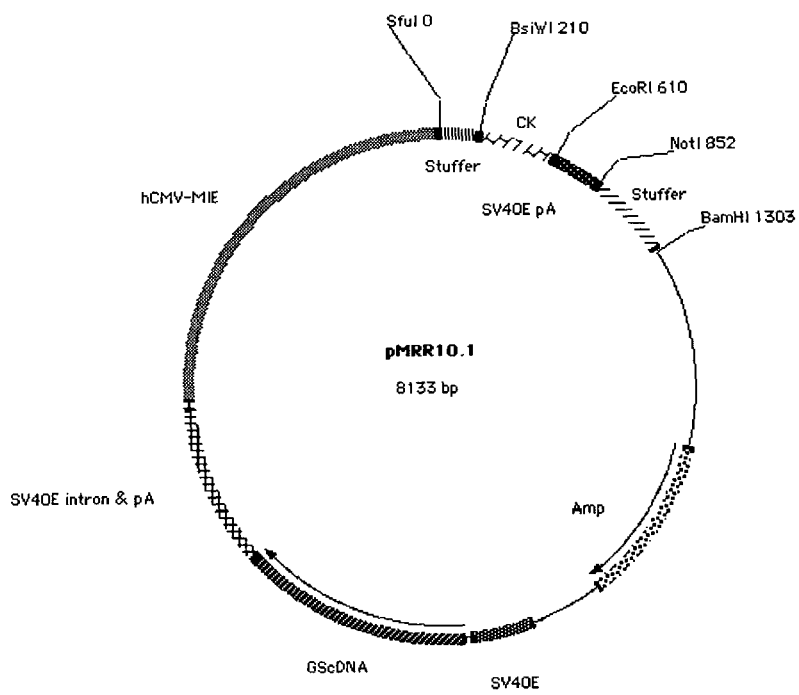

Figure 8: Biacore assay of chimeric 5/44 and mutants

| 5/44 | Ka $e^5$ | Kd $e^{-4}$ | KD $e^{-10}$ | ~KD Nm |
|------|------|------|------|------|
| cLcH | 2.9 | 1.14 | 3.93 | 0.4 |
| N55Q | 5.81 | 1.9 | 3.27 | 0.3 |
| T57A | 7.8 | 0.51 | 0.66 | 0.07 |
| K60R | 4.95 | 1.01 | 2.04 | 0.2 |

Figure 9: Oligonucleotides for 5/44 gH1 and gL1 gene assemblies

Heavy Chain

544gH1 T1

AGTGTGAGGTGCAATTGGTCCAGTCAGGAGCAGAGGTTAAGAAGCCTGGT
GCTTCCGTCAAAGTTTCGTGTAAGGCTAGCGGCTACAGGTTCAC

544gH1 T2

GTGGCATTAATCCCGGGAATCAGTACACTACATATAAAAGAAATCTAAAG
GGCAGAGCAACGCTGACCGCGGACACCTCCACAAGCACTGTCTACA

544gH1 T3

AGAGAAGGCTACGGTAATTACGGAGCCTGGTTCGCCTACTGGGGCCAGGG
TACCCTAGTCACAGTCTCCTCAGCTTCTACAAAGGGCCCAAGAAA 544 gH1 B1

GGACCAATTGCACCTCACACTGCACTCCCTTGAGAATGAGTGCCAGGAAC
ACGAGAGAGAATCCGAAGTCCATGGTGGCGGCAAGCTTTTATTC 544 gH1 B2

GATTCCCGGGATTAATGCCACCGATCCATTCCAGGCCTTGTCCCGGAGCCT
GCCTGACCCAATGAATCCAATAATTTGTGAACCTGTAGCCGCTAGC

544gH1 B3

CGTAATTACCGTAGCCTTCTCTAGTACAATAGTACACTGCGGTGTCCTCGG
ATCTCAGAGATGACAGCTCCATGTAGACAGTGCTTGTGGAGG

544gH1 F1

GAATAAAAGCTTGCCGCCACC

544gH1 R1

TTTCTTGGGCCCTTTGTAGAAG

Figure 9 (Continued)

Light Chain 544 gL1 T1

GCTTCCCGGGGTGACGTTCAAGTGACCCAGAGCCCATCCAGCCTGAGCGC
ATCTGTAGGAGACCGGGTCACCATCACTTGTAGATCC 544 gL1 T2

TATCTGCACAAACCAGGTAAAGCCCCACAATTGCTCATCTACGGAATCTC
TAACAGATTTAGTGGTGTACCAGACAGGTTCAGCGGTTCC

544gL1 T3

AGATTTCGCCACTTATTACTGTTTACAAGGTACACATCAGCCGTACACATT
CGGTCAGGGTACTAAAGTAGAAATCAAACGTACGGCGTGC

544gL1 B1

GAACGTCACCCCGGGAAGCAGGAATCCAGAACAACAGAAGCACCAACAG
CCTAACAGGCAACTTCATGGTGGCGGCTTCGAATCATCC

544gL1 B2

CTTTACCTGGTTTGTGCAGATACCAAGACAAAAAGGTGTTCCCATAACTGT
TTGCAAGACTCTGACTGGATCTACAAGTGATGGTGAC

544gL1 B3

AACAGTAATAAGTGGCGAAATCTTCTGGCTGGAGAGACGAGATCGTGAGP
GGTGAAATCAGTACCACTTCCGGAACCGCTGAACCTGTCTG

544gL1 F1

GGATGATTCGAAGCCGCCAC

544gL1 R1

GCACGCCGTACGTTTGATTTC

Figure 10: Plasmid maps of intermediate vectors pCR2.1 (544gH1) and pCR2.1(544gL1)
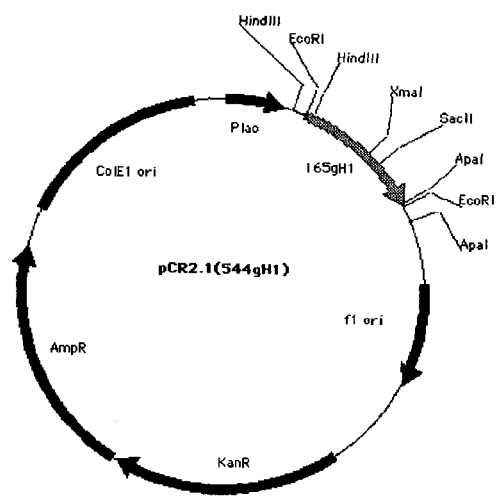
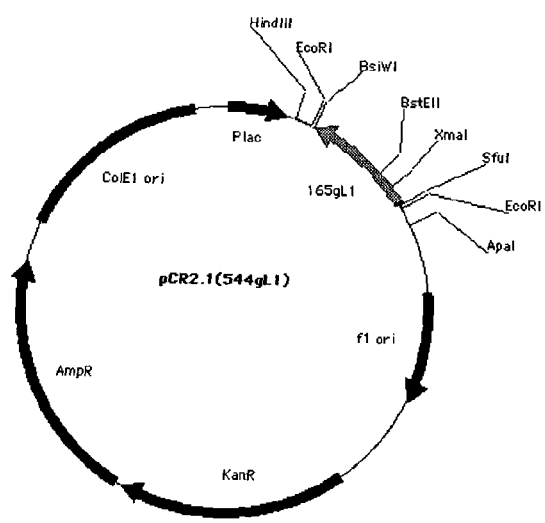

Figure 11: Oligonucleotide cassettes used to make further grafts gH4

```
    XmaI        10          20          30          40          50       SacII
    CC GGG AAT AAC TAC GCT ACA TAT AGG AGA AAT CTA AAG GGC AGA GCA ACG CTG ACC GC
           C TTA TTG ATG CGA TGT ATA TCC TCT TTA GAT TTC CCG TCT CGT TGC GAC TGG
           P   G   N   N   Y   A   T   Y   R   R   N   L   K   G   R   A   T   L   T   A
``` gH5

```
    XmaI        10          20          30          40          50       SacII
    CC GGG AAT AAC TAC GCT ACA TAT AGG AGA AAT CTA AAG GGC AGA GTT ACG ATG ACC GC
           C TTA TTG ATG CGA TGT ATA TCC TCT TTA GAT TTC CCG TCT CAA TGC TAC TGG
           P   G   N   N   Y   A   T   Y   R   R   K   F   Q   G   R   V   T   M   T   A
``` gH6

```
    XmaI        10          20          30          40          50       SacII
    CC GGG AAT AAC TAC GCT ACA TAT AGG AGA AAA TTC CAG GGC AGA GCA ACG CTG ACC GC
           C TTA TTG ATG CGA TGT ATA TCC TCT TTT AAG GTC CCG TCT CGT TGC GAC TGG
           P   G   N   N   Y   A   T   Y   R   R   K   F   Q   G   R   A   T   L   T   A
``` gH7

```
    XmaI        10          20          30          40          50       SacII
    CC GGG AAT AAC TAC GCT ACA TAT AGG AGA AAA TTC CAG GGC AGA GTT ACG ATG ACC GC
           C TTA TTG ATG CGA TGT ATA TCC TCT TTT AAG GTC CCG TCT CAA TGC TAC TGG
           P   G   N   N   Y   A   T   Y   R   R   K   F   Q   G   R   V   T   M   T   A
``` gL2

```
    XmaI      10         20         30         40         50         60      BstEII
    C CGG GGT GAC GTT GTC GTG ACC CAG AGC CCA TCC AGC CTG AGC GCA TCT GTA GGA GAC CGG
          CCA CTG CAA CAG CAC TGG GTC TCG GGT AGG TCG GAC TCG CGT AGA CAT CCT CTG GCC CAG TG
          S   R   G   D   V   V   V   T   Q   S   P   S   S   L   S   A   S   V   G   D   R   V   T
```

Figure 12: Competition assay, competing binding of fluorescently labelled mouse 5/44 antibody with grafted variants.
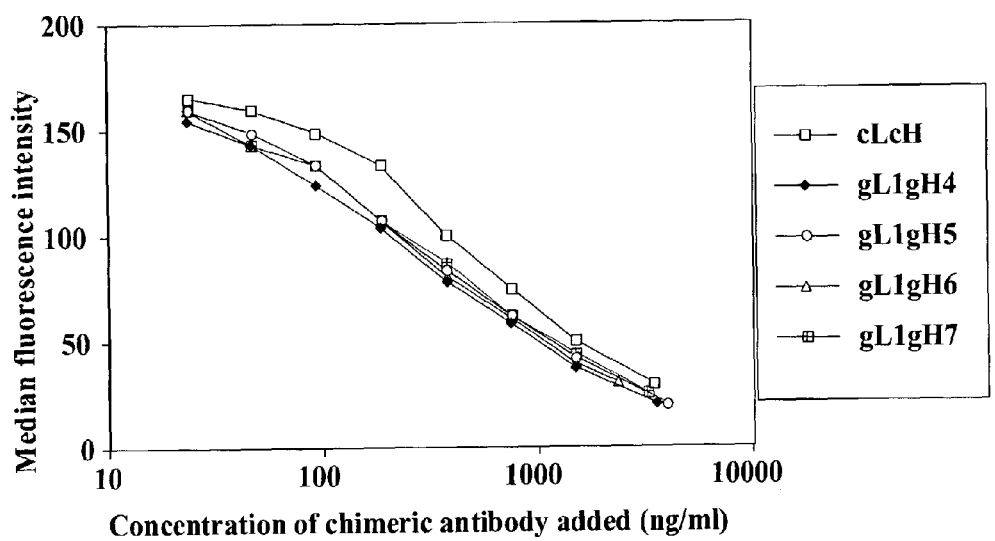
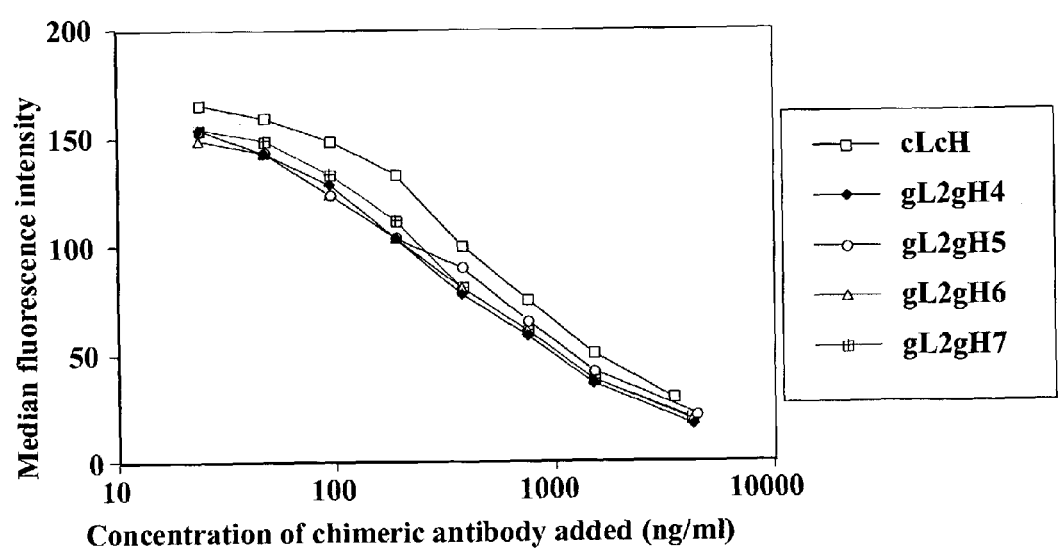

Figure 13: Full DNA sequence of grafted heavy and light chains a) Heavy Chain

```
                10         20         30         40         50         60
      AAGCTTGCCG CCACC ATG GAC TTC GGA TTC TCT CTC GTG TTC CTG GCA CTC ATT CTC AAG
      TTCGAACGGC GGTGG TAC CTG AAG CCT AAG AGA GAG CAC AAG GAC CGT GAG TAA GAG TTC
                       M   D   F   G   F   S   L   V   F   L   A   L   I   L   K>

70         80         90        100        110
           GGA GTG CAG TGT GAG GTG CAA TTG GTC CAG TCA GGA GCA GAG GTT AAG AAG CCT GGT
           CCT CAC GTC ACA CTC CAC GTT AAC CAG GTC AGT CCT CGT CTC CAA TTC TTC GGA CCA
            G   V   Q   C   E   V   Q   L   V   Q   S   G   A   E   V   K   K   P   G>

120        130        140        150        160        170
    GCT TCC GTC AAA GTT TCG TGT AAG GCT AGC GGC TAC AGG TTC ACA AAT TAT TGG ATT
    CGA AGG CAG TTT CAA AGC ACA TTC CGA TCG CCG ATG TCC AAG TGT TTA ATA ACC TAA
     A   S   V   K   V   S   C   K   A   S   G   Y   R   F   T   N   Y   W   I>

180        190        200        210        220        230
    CAT TGG GTC AGG CAG GCT CCG GGA CAA GGC CTG GAA TGG ATC GGT GGC ATT AAT CCC
    GTA ACC CAG TCC GTC CGA GGC CCT GTT CCG GAC CTT ACC TAG CCA CCG TAA TTA GGG
     H   W   V   R   Q   A   P   G   Q   G   L   E   W   I   G   G   I   N   P>

240        250        260        270        280
    GGG AAT AAC TAC GCT ACA TAT AGG AGA AAA TTC CAG GGC AGA GTT ACG ATG ACC GCG
    CCC TTA TTG ATG CGA TGT ATA TCC TCT TTT AAG GTC CCG TCT CAA TGC TAC TGG CGC
     G   N   N   Y   A   T   Y   R   R   K   F   Q   G   R   V   T   M   T   A>

290        300        310        320        330        340
    GAC ACC TCC ACA AGC ACT GTC TAC ATG GAG CTG TCA TCT CTG AGA TCC GAG GAC ACC
    CTG TGG AGG TGT TCG TGA CAG ATG TAC CTC GAC AGT AGA GAC TCT AGG CTC CTG TGG
     D   T   S   T   S   T   V   Y   M   E   L   S   S   L   R   S   E   D   T>

350        360        370        380        390        400
    GCA GTG TAC TAT TGT ACT AGA GAA GGC TAC GGT AAT TAC GGA GCC TGG TTC GCC TAC
    CGT CAC ATG ATA ACA TGA TCT CTT CCG ATG CCA TTA ATG CCT CGG ACC AAG CGG ATG
     A   V   Y   Y   C   T   R   E   G   Y   G   N   Y   G   A   W   F   A   Y>

410        420        430        440        450
    TGG GGC CAG GGT ACC CTA GTC ACA GTC TCC TCA GCT TCT ACA AAG GGC CCA TCC GTC
    ACC CCG GTC CCA TGG GAT CAG TGT CAG AGG AGT CGA AGA TGT TTC CCG GGT AGG CAG
     W   G   Q   G   T   L   V   T   V   S   S   A   S   T   K   G   P   S   V>

460        470        480        490        500        510
    TTC CCC CTG GCG CCC TGC TCC AGG AGC ACC TCC GAG AGC ACA GCC GCC CTG GGC TGC
    AAG GGG GAC CGC GGG ACG AGG TCC TCG TGG AGG CTC TCG TGT CGG CGG GAC CCG ACG
     F   P   L   A   P   C   S   R   S   T   S   E   S   T   A   A   L   G   C>
```

Figure 13 (Continued)

```
        520         530         540         550         560         570
CTG GTC AAG GAC TAC TTC CCC GAA CCG GTG ACG GTG TCG TGG AAC TCA GGC GCC CTG
GAC CAG TTC CTG ATG AAG GGG CTT GGC CAC TGC CAC AGC ACC TTG AGT CCG CGG GAC
 L   V   K   D   Y   F   P   E   P   V   T   V   S   W   N   S   G   A   L>

580         590         600         610         620         630
ACC AGC GGC GTG CAC ACC TTC CCG GCT GTC CTA CAG TCC TCA GGA CTC TAC TCC CTC
TGG TCG CCG CAC GTG TGG AAG GGC CGA CAG GAT GTC AGG AGT CCT GAG ATG AGG GAG
 T   S   G   V   H   T   F   P   A   V   L   Q   S   S   G   L   Y   S   L>

640         650         660         670         680
AGC AGC GTG GTG ACC GTG CCC TCC AGC AGC TTG GGC ACG AAG ACC TAC ACC TGC AAC
TCG TCG CAC CAC TGG CAC GGG AGG TCG TCG AAC CCG TGC TTC TGG ATG TGG ACG TTG
 S   S   V   V   T   V   P   S   S   S   L   G   T   K   T   Y   T   C   N>

690         700         710         720         730         740
GTA GAT CAC AAG CCC AGC AAC ACC AAG GTG GAC AAG AGA GTT G GTGAGAGGCC
CAT CTA GTG TTC GGG TCG TTG TGG TTC CAC CTG TTC TCT CAA C CACTCTCCGG
 V   D   H   K   P   S   N   T   K   V   D   K   R   V>

750         760         770         780         790         800         810
AGCACAGGGA GGGAGGGTGT CTGCTGGAAG CCAGGCTCAG CCCTCCTGCC TGGACGCACC CCGGCTGTGC
TCGTGTCCCT CCCTCCCACA GACGACCTTC GGTCCGAGTC GGGAGGACGG ACCTGCGTGG GGCCGACACG 820         830         840         850         860         870         880
AGCCCCAGCC CAGGGCAGCA AGGCATGCCC CATCTGTCTC CTCACCCGGA GGCCTCTGAC CACCCCACTC
TCGGGGTCGG GTCCCGTCGT TCCGTACGGG GTAGACAGAG GAGTGGGCCT CCGGAGACTG GTGGGGTGAG 890         900         910         920         930         940         950
ATGCCCAGGG AGAGGGTCTT CTGGATTTTT CCACCAGGCT CCGGGCAGCC ACAGGCTGGA TGCCCCTACC
TACGGGTCCC TCTCCCAGAA GACCTAAAAA GGTGGTCCGA GGCCCGTCGG TGTCCGACCT ACGGGGATGG 960         970         980         990         1000        1010        1020
CCAGGCCCTG CGCATACAGG GGCAGGTGCT GCGCTCAGAC CTGCCAAGAG CCATATCCGG GAGGACCCTG
GGTCCGGGAC GCGTATGTCC CCGTCCACGA CGCGAGTCTG GACGGTTCTC GGTATAGGCC CTCCTGGGAC 1030        1040        1050        1060        1070        1080        1090
CCCCTGACCT AAGCCCACCC CAAAGGCCAA ACTCTCCACT CCCTCAGCTC AGACACCTTC TCTCCTCCCA
GGGGACTGGA TTCGGGTGGG GTTTCCGGTT TGAGAGGTGA GGGAGTCGAG TCTGTGGAAG AGAGGAGGGT 1100        1110        1120        1130        1140        1150
GATCTGAGTA ACTCCCAATC TTCTCTCTGC A GAG TCC AAA TAT GGT CCC CCA TGC CCA CCA
CTAGACTCAT TGAGGGTTAG AAGAGAGACG T CTC AGG TTT ATA CCA GGG GGT ACG GGT GGT
                                    E   S   K   Y   G   P   P   C   P   P>
```

Figure 13 (Continued)

```
      1160       1170       1180       1190       1200       1210       1220
   TGC CCA GGT AAGCCAACCC AGGCCTCGCC CTCCAGCTCA AGGCGGGACA GGTGCCCTAG AGTAGCCTGC
   ACG GGT CCA TTCGGTTGGG TCCGGAGCGG GAGGTCGAGT TCCGCCCTGT CCACGGGATC TCATCGGACG
    C   P>

1230       1240       1250       1260       1270       1280
ATCCAGGGAC AGGCCCCAGC CGGGTGCTGA CGCATCCACC TCCATCTCTT CCTCA GCA CCT GAG TTC
TAGGTCCCTG TCCGGGGTCG GCCCACGACT GCGTAGGTGG AGGTAGAGAA GGAGT CGT GGA CTC AAG
                                                             A   P   E   F>

1290       1300       1310       1320       1330       1340
   CTG GGG GGA CCA TCA GTC TTC CTG TTC CCC CCA AAA CCC AAG GAC ACT CTC ATG ATC
   GAC CCC CCT GGT AGT CAG AAG GAC AAG GGG GGT TTT GGG TTC CTG TGA GAG TAC TAG
    L   G   G   P   S   V   F   L   F   P   P   K   P   K   D   T   L   M   I>

1350       1360       1370       1380       1390       1400
   TCC CGG ACC CCT GAG GTC ACG TGC GTG GTG GTG GAC GTG AGC CAG GAA GAC CCC GAG
   AGG GCC TGG GGA CTC CAG TGC ACG CAC CAC CAC CTG CAC TCG GTC CTT CTG GGG CTC
    S   R   T   P   E   V   T   C   V   V   V   D   V   S   Q   E   D   P   E>

1410       1420       1430       1440       1450
   GTC CAG TTC AAC TGG TAC GTG GAT GGC GTG GAG GTG CAT AAT GCC AAG ACA AAG CCG
   CAG GTC AAG TTG ACC ATG CAC CTA CCG CAC CTC CAC GTA TTA CGG TTC TGT TTC GGC
    V   Q   F   N   W   Y   V   D   G   V   E   V   H   N   A   K   T   K   P>

1460       1470       1480       1490       1500       1510
   CGG GAG GAG CAG TTC AAC AGC ACG TAC CGT GTG GTC AGC GTC CTC ACC GTC CTG CAC
   GCC CTC CTC GTC AAG TTG TCG TGC ATG GCA CAC CAG TCG CAG GAG TGG CAG GAC GTG
    R   E   E   Q   F   N   S   T   Y   R   V   V   S   V   L   T   V   L   H>

1520       1530       1540       1550       1560       1570
   CAG GAC TGG CTG AAC GGC AAG GAG TAC AAG TGC AAG GTC TCC AAC AAA GGC CTC CCG
   GTC CTG ACC GAC TTG CCG TTC CTC ATG TTC ACG TTC CAG AGG TTG TTT CCG GAG GGC
    Q   D   W   L   N   G   K   E   Y   K   C   K   V   S   N   K   G   L   P>

1580       1590       1600       1610       1620       1630
   TCC TCC ATC GAG AAA ACC ATC TCC AAA GCC AAA GGTGG GACCCACGGG GTGCGAGGGC
   AGG AGG TAG CTC TTT TGG TAG AGG TTT CGG TTT CCACC CTGGGTGCCC CACGCTCCCG
    S   S   I   E   K   T   I   S   K   A   K>

1640       1650       1660       1670       1680       1690       1700
CACATGGACA GAGGTCAGCT CGGCCCACCC TCTGCCCTGG GAGTGACCGC TGTGCCAACC TCTGTCCCTA
GTGTACCTGT CTCCAGTCGA GCCGGGTGGG AGACGGGACC CTCACTGGCG ACACGGTTGG AGACAGGGAT
```

Figure 13 (Continued)

```
         1710        1720       1730       1740       1750
CA GGG CAG CCC CGA GAG CCA CAG GTG TAC ACC CTG CCC CCA TCC CAG GAG GAG ATG
GT CCC GTC GGG GCT CTC GGT GTC CAC ATG TGG GAC GGG GGT AGG GTC CTC CTC TAC
    G   Q   P   R   E   P   Q   V   Y   T   L   P   P   S   Q   E   E   M>

1760       1770       1780       1790       1800       1810
ACC AAG AAC CAG GTC AGC CTG ACC TGC CTG GTC AAA GGC TTC TAC CCC AGC GAC ATC
TGG TTC TTG GTC CAG TCG GAC TGG ACG GAC CAG TTT CCG AAG ATG GGG TCG CTG TAG
 T   K   N   Q   V   S   L   T   C   L   V   K   G   F   Y   P   S   D   I>

1820       1830       1840       1850       1860       1870
GCC GTG GAG TGG GAG AGC AAT GGG CAG CCG GAG AAC AAC TAC AAG ACC ACG CCT CCC
CGG CAC CTC ACC CTC TCG TTA CCC GTC GGC CTC TTG TTG ATG TTC TGG TGC GGA GGG
 A   V   E   W   E   S   N   G   Q   P   E   N   N   Y   K   T   T   P   P>

1880       1890       1900       1910       1920
GTG CTG GAC TCC GAC GGC TCC TTC TTC CTC TAC AGC AGG CTA ACC GTG GAC AAG AGC
CAC GAC CTG AGG CTG CCG AGG AAG AAG GAG ATG TCG TCC GAT TGG CAC CTG TTC TCG
 V   L   D   S   D   G   S   F   F   L   Y   S   R   L   T   V   D   K   S>

1930       1940       1950       1960       1970       1980
AGG TGG CAG GAG GGG AAT GTC TTC TCA TGC TCC GTG ATG CAT GAG GCT CTG CAC AAC
TCC ACC GTC CTC CCC TTA CAG AAG AGT ACG AGG CAC TAC GTA CTC CGA GAC GTG TTG
 R   W   Q   E   G   N   V   F   S   C   S   V   M   H   E   A   L   H   N>

1990       2000       2010       2020       2030       2040
CAC TAC ACA CAG AAG AGC CTC TCC CTG TCT CTG GGT AAA TGA GTGC CAGGGCCGGC
GTG ATG TGT GTC TTC TCG GAG AGG GAC AGA GAC CCA TTT ACT CACG GTCCCGGCCG
 H   Y   T   Q   K   S   L   S   L   S   L   G   K   *>

2050       2060       2070       2080       2090       2100       2110
AAGCCCCCGC TCCCCGGGCT CTCGGGGTCG CGCGAGGATG CTTGGCACGT ACCCCGTCTA CATACTTCCC
TTCGGGGGCG AGGGGCCCGA GAGCCCCAGC GCGCTCCTAC GAACCGTGCA TGGGGCAGAT GTATGAAGGG 2120       2130       2140       2150       2160
AGGCACCCAG CATGGAAATA AAGCACCCAC CACTGCCCTG GCTCGAATTC
TCCGTGGGTC GTACCTTTAT TTCGTGGGTG GTGACGGGAC CGAGCTTAAG
```

Figure 13 (Continued)

b) Light Chain

```
            10         20         30         40         50         60
TTCGAAGCCG CCACC ATG AAG TTG CCT GTT AGG CTG TTG GTG CTT CTG TTG TTC TGG ATT
AAGCTTCGGC GGTGG TAC TTC AAC GGA CAA TCC GAC AAC CAC GAA GAC AAC AAG ACC TAA
                  M   K   L   P   V   R   L   L   V   L   L   L   F   W   I>

70         80         90        100        110
CCT GCT TCC CGG GGT GAC GTT CAA GTG ACC CAG AGC CCA TCC AGC CTG AGC GCA TCT
GGA CGA AGG GCC CCA CTG CAA GTT CAC TGG GTC TCG GGT AGG TCG GAC TCG CGT AGA
 P   A   S   R   G   D   V   Q   V   T   Q   S   P   S   S   L   S   A   S>

120        130        140        150        160        170
GTA GGA GAC CGG GTC ACC ATC ACT TGT AGA TCC AGT CAG AGT CTT GCA AAC AGT TAT
CAT CCT CTG GCC CAG TGG TAG TGA ACA TCT AGG TCA GTC TCA GAA CGT TTG TCA ATA
 V   G   D   R   V   T   I   T   C   R   S   S   Q   S   L   A   N   S   Y>

180         190        200        210         220        230
GGG AAC ACC TTT TTG TCT TGG TAT CTG CAC AAA CCA GGT AAA GCC CCA CAA TTG CTC
CCC TTG TGG AAA AAC AGA ACC ATA GAC GTG TTT GGT CCA TTT CGG GGT GTT AAC GAG
 G   N   T   F   L   S   W   Y   L   H   K   P   G   K   A   P   Q   L   L>

240        250        260        270        280
ATC TAC GGA ATC TCT AAC AGA TTT AGT GGT GTA CCA GAC AGG TTC AGC GGT TCC GGA
TAG ATG CCT TAG AGA TTG TCT AAA TCA CCA CAT GGT CTG TCC AAG TCG CCA AGG CCT
 I   Y   G   I   S   N   R   F   S   G   V   P   D   R   F   S   G   S   G>

290        300        310        320        330        340
AGT GGT ACT GAT TTC ACC CTC ACG ATC TCG TCT CTC CAG CCA GAA GAT TTC GCC ACT
TCA CCA TGA CTA AAG TGG GAG TGC TAG AGC AGA GAG GTC GGT CTT CTA AAG CGG TGA
 S   G   T   D   F   T   L   T   I   S   S   L   Q   P   E   D   F   A   T>

350        360        370        380        390        400
TAT TAC TGT TTA CAA GGT ACA CAT CAG CCG TAC ACA TTC GGT CAG GGT ACT AAA GTA
ATA ATG ACA AAT GTT CCA TGT GTA GTC GGC ATG TGT AAG CCA GTC CCA TGA TTT CAT
 Y   Y   C   L   Q   G   T   H   Q   P   Y   T   F   G   Q   G   T   K   V>

410        420        430        440        450
GAA ATC AAA CGT ACG GTA GCG GCC CCA TCT GTC TTC ATC TTC CCG CCA TCT GAT GAG
CTT TAG TTT GCA TGC CAT CGC CGG GGT AGA CAG AAG TAG AAG GGC GGT AGA CTA CTC
 E   I   K   R   T   V   A   A   P   S   V   F   I   F   P   P   S   D   E>

460        470        480        490        500        510
CAG TTG AAA TCT GGA ACT GCC TCT GTT GTG TGC CTG CTG AAT AAC TTC TAT CCC AGA
GTC AAC TTT AGA CCT TGA CGG AGA CAA CAC ACG GAC GAC TTA TTG AAG ATA GGG TCT
 Q   L   K   S   G   T   A   S   V   V   C   L   L   N   N   F   Y   P   R>
```

Figure 13 (Continued)

```
         520         530         540         550         560         570
        GAG GCC AAA GTA CAG TGG AAG GTG GAT AAC GCC CTC CAA TCG GGT AAC TCC CAG GAG
        CTC CGG TTT CAT GTC ACC TTC CAC CTA TTG CGG GAG GTT AGC CCA TTG AGG GTC CTC
         E   A   K   V   Q   W   K   V   D   N   A   L   Q   S   G   N   S   Q   E>

580         590         600         610         620         630
        AGT GTC ACA GAG CAG GAC AGC AAG GAC AGC ACC TAC AGC CTC AGC AGC ACC CTG ACG
        TCA CAG TGT CTC GTC CTG TCG TTC CTG TCG TGG ATG TCG GAG TCG TCG TGG GAC TGC
         S   V   T   E   Q   D   S   K   D   S   T   Y   S   L   S   S   T   L   T>

640         650         660         670         680
        CTG AGC AAA GCA GAC TAC GAG AAA CAC AAA GTC TAC GCC TGC GAA GTC ACC CAT CAG
        GAC TCG TTT CGT CTG ATG CTC TTT GTG TTT CAG ATG CGG ACG CTT CAG TGG GTA GTC
         L   S   K   A   D   Y   E   K   H   K   V   Y   A   C   E   V   T   H   Q>

690         700         710         720         730         740
        GGC CTG AGC TCG CCC GTC ACA AAG AGC TTC AAC AGG GGA GAG TGT TAG AGGGA
        CCG GAC TCG AGC GGG CAG TGT TTC TCG AAG TTG TCC CCT CTC ACA ATC TCCCT
         G   L   S   S   P   V   T   K   S   F   N   R   G   E   C   *>

750         760         770         780
        GAAGTGCCCC CACCTGCTCC TCAGTTCCAG CCTGGGAATT C
        CTTCACGGGG GTGGACGAGG AGTCAAGGTC GGACCCTTAA G
```

BIOLOGICAL PRODUCTS

This application claims priority under 35 U.S.C. §119(a)-(d) to United Kingdom Application No. GB 0210121.0, filed May 2, 2002, and the application hereby is incorporated by reference in its entirety.

The present invention relates to an antibody molecule having specificity for antigenic determinants of the B lymphocyte antigen, CD22. The present invention also relates to the therapeutic uses of the antibody molecule and methods for producing the antibody molecule.

In a natural antibody molecule, there are two heavy chains and two light chains. Each heavy chain and each light chain has at its N-terminal end a variable domain. Each variable domain is composed of four framework regions (FRs) alternating with three complementarity determining regions (CDRs). The residues in the variable domains are conventionally numbered according to a system devised by Kabat et al. This system is set forth in Kabat et al, 1987, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or CDR, of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering.

The CDRs of the light chain variable domain are located at residues 24-34 (CDR-L1), residues 50-56 (CDR-L2) and residues 89-97 (CDR-L3) according to the Kabat numbering.

Construction of CDR-grafted antibodies is described in European Patent Application EP-A-0239400, which discloses a process in which the CDRs of a mouse monoclonal antibody are grafted onto the framework regions of the variable domains of a human immunoglobulin by site directed mutagenesis using long oligonucleotides. The CDRs determine the antigen binding specificity of antibodies and are relatively short peptide sequences carried on the framework regions of the variable domains.

The earliest work on humanising monoclonal antibodies by CDR-grafting was carried out on monoclonal antibodies recognising synthetic antigens, such as NP. However, examples in which a mouse monoclonal antibody recognising lysozyme and a rat monoclonal antibody recognising an antigen on human T-cells were humanised by CDR-grafting have been described by Verhoeyen et al. (Science, 239, 1534-1536, 1988) and Riechmann et al. (Nature, 332, 323-324, 1988), respectively.

Riechmann et al., found that the transfer of the CDRs alone (as defined by Kabat (Kabat et al. (supra) and Wu et al., J. Exp. Med., 132, 211-250, 1970)) was not sufficient to provide satisfactory antigen binding activity in the CDR-grafted product. It was found that a number of framework residues have to be altered so that they correspond to those of the donor framework region. Proposed criteria for selecting which framework residues need to be altered are described in International Patent Application No. WO 90/07861.

A number of reviews discussing CDR-grafted antibodies have been published, including Vaughan et al. (Nature Biotechnology, 16, 535-539, 1998).

Malignant lymphomas are a diverse group of neoplasms. The majority of cases occur in older people. Non-Hodgkins Lymphoma (NHL) is a disease that currently affects 200,000 to 250,000 patients in the U.S. It is the second fastest rising cancer in the U.S., rising at a rate of about 55,000 new cases per year. The incidence is rising at a rate that is greater than can be accounted for simply by the increasing age of the population and exposure to known risk factors.

The classification of lymphoma is complex, and has evolved in recent decades. In 1994 the Revised European-American Lymphoma (REAL) classification was introduced. This classification organises lymphomas of B cell (the most frequently identified), T cell and unclassifiable origin into agreed subtypes. In everyday practice, the grouping of NHLs into low, intermediate and high-grade categories on the basis of their general histological appearance, broadly reflects their clinical behaviour.

NHL predominantly affects the lymph nodes but, in individual patients, the tumour may involve other anatomical sites such as the liver, spleen, bone marrow, lung, gut and skin. The disease commonly presents as a painless enlargement of lymph nodes. Extranodal lymphoma most frequently affects the gut, although primary lymphoma of virtually every organ has been documented. Systemic symptoms include fever, sweats, tiredness and weight loss.

Until recently, the Ann Arbor staging system, based entirely upon the anatomical extent of disease, was the major determinant of therapy in NHL. This information may be refined by incorporating additional prognostic pointers, including age, serum lactate dehydrogenase levels and performance status. Even so, knowledge of the Ann Arbor staging system, together with the histological and immunological subtype of the tumour, is still the major determinant of treatment.

Low grade NHL has an indolent course, with a median patient survival of 8 to 10 years. Survival is little impacted by currently available therapy, although irradiation of local disease and chemotherapy for systemic symptoms improves patients' quality of life. Combination chemotherapy may be reserved for relapsed disease. Intermediate disease and, especially, high grade disease is extremely aggressive and tends to disseminate. Disease of this grade requires urgent treatment. Radiotherapy may be a useful component of treatment in patients with very bulky disease. Many different chemotherapy regimens have been employed, and long-term disease-free survival may be obtained in more than half of patients. High dose therapy with stem cell support was introduced initially for patients with relapsed or refractory disease, but is now increasingly finding a place in first line therapy for patients with poor-risk disease. The tendency in recent years for an increasingly aggressive therapeutic approach must be balanced against the generally elderly age and relative debility of many patients with NHL, and by the need to match the toxicity of treatment to the individual prognosis of each patient's disease.

Improved treatments, that are more effective and better tolerated, are needed. Agents recently introduced include new cytotoxic drugs, progressively incorporated into combinations, and the introduction of antibody-based therapies.

Non-Hodgkin's lymphoma encompasses a range of B cell lymphomas. B cell antigens therefore represent suitable targets for antibody therapy.

CD22 is a 135 kDa membrane glycoprotein belonging to a family of sialic acid binding proteins called sialoadhesins. It is detected in the cytoplasm early in B cell development, appears on the cell surface simultaneously with IgD and is found on most mature B cells. Expression is increased following B cell activation. CD22 is lost with terminal differentiation and is generally reported as being absent on plasma cells. Thus this internalising antigen is present on the surface of pre-B cells and mature B cells but not stem cells or plasma cells.

Two isoforms of CD22 exist in man. The predominant form (CD22β) contains 7 immunoglobulin-like (Ig-like) domains in the extracellular region. The CD22α variant lacks Ig-like domain 4 and may have a truncated cytoplasmic domain. Antibodies which block CD22 adhesion to monocytes, neutrophils, lymphocytes and erythrocytes have been shown to bind within the first or second Ig-like domain.

The cytoplasmic domain of CD22 is tyrosine phosphorylated upon ligation of the B cell antigen receptor and associates with Lyk, Syk and phosphatidyl inositol 3-kinase. The function of CD22 is to down-modulate the B cell activation threshold. It can also mediate cell adhesion through interaction with cells bearing the appropriate sialoglycoconjugates.

CD22 is expressed in most B cell leukaemias and lymphomas, including NHL, acute lymphoblastic leukaemia (B-ALL), chronic lymphocytic leukaemia (B-CLL) and especially acute non-lymphocytic leukaemia (ANLL).

Monoclonal antibodies against CD22 have been described in the prior art. WO 98/41641 describes recombinant anti-CD22 antibodies with cysteine residues at $V_H44$ and $V_L100$. WO 96/04925 describes the $V_H$ and $V_L$ regions of the anti-CD22 antibody LL2. U.S. Pat. No. 5,686,072 describes combinations of anti-CD22 and anti-CD19 immunotoxins. WO 98/42378 describes the use of naked anti-CD22 antibodies for the treatment of B-cell malignancies.

A number of antibody-based therapeutics have either been recently licensed, e.g. Rituxan (an unlabelled chimeric human γ1 (+mγ1V-region) specific for CD20), or are in clinical trials for this disease. These rely either on complement- or ADCC-mediated killing of B cells or the use of radionuclides, such as $^{131}I$ or $^{90}Y$, which have associated preparation and use problems for clinicians and patients. There is a need for an antibody molecule to treat NHL which can be used repeatedly and produced easily and efficiently. There is also a need for an antibody molecule, which has high affinity for CD22 and low immunogenicity in humans.

SUMMARY OF THE INVENTION

In a first aspect, the present invention provides an antibody molecule having specificity for human CD22, comprising a heavy chain wherein the variable domain comprises a CDR (as defined by Kabat et al., (supra)) having the sequence given as H1 in FIG. 1 (SEQ ID NO:1) for CDR-H1, as H2 in FIG. 1 (SEQ ID NO:2) or an H2 from which a potential glycosylation site has been removed, or an H2 in which the lysine residue at position 60 (according to the Kabat numbering system) has been replaced by an alternative amino acid, or an H2 in which both the glycosylation site and the reactive lysine at position 60 have been removed for CDR-H2 or as H3 in FIG. 1 (SEQ ID NO:3) for CDR-H3.

The antibody molecule of the first aspect of the present invention comprises at least one CDR selected from H1, H2 and H3 (SEQ ID NO:1, SEQ ID NO:2 and SEQ ID NO:3) for the heavy chain variable domain. Preferably, the antibody molecule comprises at least two and more preferably all three CDRs in the heavy chain variable domain.

In a second aspect of the present invention, there is provided an antibody molecule having specificity for human CD22, comprising a light chain wherein the variable domain comprises a CDR (as defined by Kabat et al., (supra)) having the sequence given as L1 in FIG. 1 (SEQ ID NO:4) for CDR-L1, L2 in FIG. 1 (SEQ ID NO:5) for CDR-L2 or L3 in FIG. 1 (SEQ ID NO:6) for CDR-L3.

The antibody molecule of the second aspect of the present invention comprises at least one CDR selected from L1, L2 and L3 (SEQ ID NO:4; SEQ ID NO:5 and SEQ ID NO:6) for the light chain variable domain. Preferably, the antibody molecule comprises at least two and more preferably all three CDRs in the light chain variable domain.

The antibody molecules of the first and second aspects of the present invention preferably have a complementary light chain or a complementary heavy chain, respectively.

Preferably, the antibody molecule of the first or second aspect of the present invention comprises a heavy chain wherein the variable domain comprises a CDR (as defined by Kabat et al., (supra)) having the sequence given as H1 in FIG. 1 (SEQ ID NO:1) for CDR-H1, as H2 in FIG. 1 (SEQ ID NO:2) or an H2 from which a potential glycosylation site has been removed, or an H2 in which the lysine residue at position 60 (according to the Kabat numbering system) has been replaced by an alternative amino acid, or an H2 in which both the glycosylation site and the reactive lysine at position 60 have been removed for CDR-H2 or as H3 in FIG. 1 (SEQ ID NO:3) for CDR-H3 and a light chain wherein the variable domain comprises a CDR (as defined by Kabat et al., (supra)) having the sequence given as L1 in FIG. 1 (SEQ ID NO:4) for CDR-L1, as L2 in FIG. 1 (SEQ ID NO:5) for CDR-L2 or as L3 in FIG. 1 (SEQ ID NO:6) for CDR-L3.

The CDRs given in SEQ IDS NOS:1 to 6 and in FIG. 1 referred to above are derived from a mouse monoclonal antibody 5/44.

The complete sequences of the variable domains of the mouse 5/44 antibody are shown in FIG. 2 (light chain) (SEQ ID NO:7) and FIG. 3 (heavy chain) (SEQ ID NO:8). This mouse antibody is also referred to below as "the donor antibody" or the "murine monoclonal antibody".

A first alternatively preferred embodiment of the first or second aspect of the present invention is the mouse monoclonal antibody 5/44 having the light and heavy chain variable domain sequences shown in FIG. 2 (SEQ ID NO:7) and FIG. 3 (SEQ ID NO:8), respectively. The light chain constant region of 5/44 is kappa and the heavy chain constant region is IgG1.

In a second alternatively preferred embodiment, the antibody according to either of the first and second aspects of the present invention is a chimeric mouse/human antibody molecule, referred to herein as the chimeric 5/44 antibody molecule. The chimeric antibody molecule comprises the variable domains of the mouse monoclonal antibody 5/44 (SEQ ID NOS:7 and 8) and human constant domains. Preferably, the chimeric 5/44 antibody molecule comprises the human C kappa domain (Hieter et al., Cell, 22, 197-207, 1980; Genebank accession number J00241) in the light chain and the human gamma 4 domains (Flanagan et al., Nature, 300, 709-713, 1982) in the heavy chain, optionally with the serine residue at position 241 replaced by a proline residue.

Preferably, the antibody of the present invention comprises a heavy chain wherein the variable domain comprises as CDR-H2 (as defined by Kabat et al., (supra)) an H2' in which a potential glycosylation site sequence has been removed and which unexpectedly increased the affinity of the chimeric 5/44 antibody for the CD22 antigen and which preferably has as CDR-H2 the sequence given as H2' (SEQ ID NO:13).

Alternatively or additionally, the antibody of the present invention may comprise a heavy chain wherein the variable domain comprises as CDR-H2 (as defined by Kabat et al., (supra)) an H2" in which a lysine residue at position 60, which is located at an exposed position within CDR-H2 and which is considered to have the potential to react with conjugation agents resulting in a reduction of antigen binding affinity, is substituted for an alternative amino acid to result in a conserved substitution. Preferably CDR-H2 has the sequence given as H2" (SEQ ID NO:15).

Alternatively or additionally, the antibody of the present invention may comprise a heavy chain wherein the variable domain comprises as CDR-H2 (as defined by Kabat et al., (supra)) an H2'" in which both the potential glycosylation site sequence and the lysine residue at position 60, are substituted for alternative amino acids. Preferably CDR-H2 has the sequence given as H2'" (SEQ ID NO:16).

In a third alternatively preferred embodiment, the antibody according to either of the first and second aspects of the present invention is a CDR-grafted antibody molecule. The term "a CDR-grafted antibody molecule" as used herein refers to an antibody molecule wherein the heavy and/or light chain contains one or more CDRs (including, if desired, a modified CDR) from a donor antibody (e.g. a murine monoclonal antibody) grafted into a heavy and/or light chain variable region framework of an acceptor antibody (e.g. a human antibody).

Preferably, such a CDR-grafted antibody has a variable domain comprising human acceptor framework regions as well as one or more of the donor CDRs referred to above.

When the CDRs are grafted, any appropriate acceptor variable region framework sequence may be used having regard to the class/type of the donor antibody from which the CDRs are derived, including mouse, primate and human framework regions. Examples of human frameworks which can be used in the present invention are KOL, NEWM, REI, EU, TUR, TEI, LAY and POM (Kabat et al. (supra)). For example, KOL and NEWM can be used for the heavy chain, REI can be used for the light chain and EU, LAY and POM can be used for both the heavy chain and the light chain. Alternatively, human germline sequences may be used. The preferred framework region for the light chain is the human germline sub-group sequence (DPK9+JK1) shown in FIG. 5 (SEQ ID NO:17). The preferred framework region for the heavy chain is the human sub-group sequence (DP7+JH4) shown in FIG. 6 (SEQ ID NO:21).

In a CDR-grafted antibody of the present invention, it is preferred to use as the acceptor antibody one having chains which are homologous to the chains of the donor antibody. The acceptor heavy and light chains do not necessarily need to be derived from the same antibody and may, if desired, comprise composite chains having framework regions derived from different chains.

Also, in a CDR-grafted antibody of the present invention, the framework regions need not have exactly the same sequence as those of the acceptor antibody. For instance, unusual residues may be changed to more frequently-occurring residues for that acceptor chain class or type. Alternatively, selected residues in the acceptor framework regions may be changed so that they correspond to the residue found at the same position in the donor antibody or to a residue that is a conservative substitution for the residue found at the same position in the donor antibody. Such changes should be kept to the minimum necessary to recover the affinity of the donor antibody. A protocol for selecting residues in the acceptor framework regions which may need to be changed is set forth in WO 91/09967.

Preferably, in a CDR-grafted antibody molecule according to the present invention, if the acceptor light chain has the human sub-group DPK9+JK1 sequence (shown in FIG. 2) (SEQ ID NO:17) then the acceptor framework regions of the light chain comprise donor residues at positions 2, 4, 37, 38, 45 and 60 and may additionally comprise a donor residue at position 3 (according to Kabat et al. (supra)).

Preferably, in a CDR-grafted antibody molecule of the present invention, if the acceptor heavy chain has the human DP7+JH4 sequence (shown in FIG. 3) (SEQ ID NO:21), then the acceptor framework regions of the heavy chain comprise, in addition to one or more donor CDRs, donor residues at positions 1, 28, 48, 71 and 93 and may additionally comprise donor residues at positions 67 and 69 (according to Kabat et al. (supra)).

Donor residues are residues from the donor antibody, i.e. the antibody from which the CDRs were originally derived.

Preferably, the antibody of the present invention comprises a heavy chain wherein the variable domain comprises as CDR-H2 (as defined by Kabat et al., (supra)) an H2' in which a potential glycosylation site sequence has been removed in order to increase the affinity of the chimeric 5/44 antibody for the CD22 antigen and which preferably has as CDR-H2 the sequence given as H2' (SEQ ID NO:13).

Alternatively or additionally, the antibody of the present invention may comprise a heavy chain wherein the variable domain comprises as CDR-H2 (as defined by Kabat et al., (supra)) an H2" in which a lysine residue at position 60, which is located at an exposed position within CDR-H2 and which is considered to have the potential to react with conjugation agents resulting in a reduction of antigen binding affinity, is substituted for an alternative amino acid. Preferably CDR-H2 has the sequence given as H2" (SEQ ID NO:15).

Alternatively or additionally, the antibody of the present invention may comprise a heavy chain wherein the variable domain comprises as CDR-H2 (as defined by Kabat et al., (supra)) an H2'" in which both the potential glycosylation site sequence and the lysine residue at position 60, are substituted for alternative amino acids. Preferably CDR-H2 has the sequence given as H2'" (SEQ ID NO:16).

The antibody molecule of the present invention may comprise: a complete antibody molecule, having full length heavy and light chains; a fragment thereof, such as a Fab, modified Fab, Fab', F(ab')$_2$ or Fv fragment; a light chain or heavy chain monomer or dimer; a single chain antibody, e.g. a single chain Fv in which the heavy and light chain variable domains are joined by a peptide linker. Similarly, the heavy and light chain variable regions may be combined with other antibody domains as appropriate.

The antibody molecule of the present invention may have an effector or a reporter molecule attached to it. For instance, it may have a macrocycle, for chelating a heavy metal atom, or a toxin, such as ricin, attached to it by a covalent bridging structure. Alternatively, procedures of recombinant DNA technology may be used to produce an antibody molecule in which the Fc fragment (CH2, CH3 and hinge domains), the CH2 and CH3 domains or the CH3 domain of a complete immunoglobulin molecule has (have) been replaced by, or has (have) attached thereto by peptide linkage, a functional non-immunoglobulin protein, such as an enzyme or toxin molecule.

The antibody molecule of the present invention preferably has a binding affinity of at least $0.85 \times 10^{-10}$ M, more preferably at least $0.75 \times 10^{-10}$ M and most preferably at least $0.5 \times 10^{-10}$ M.

Preferably, the antibody molecule of the present invention comprises the light chain variable domain 5/44-gL1 (SEQ ID NO:19) and the heavy chain variable domain 5/44-gH7 (SEQ ID NO:27). The sequences of the variable domains of these light and heavy chains are shown in FIGS. 5 and 6, respectively.

The present invention also relates to variants of the antibody molecule of the present invention, which have an improved affinity for CD22. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of *E. coli* (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

The present invention also provides a DNA sequence encoding the heavy and/or light chain(s) of the antibody molecule of the present invention.

Preferably, the DNA sequence encodes the heavy or the light chain of the antibody molecule of the present invention.

The DNA sequence of the present invention may comprise synthetic DNA, for instance produced by chemical processing, cDNA, genomic DNA or any combination thereof.

The present invention also relates to a cloning or expression vector comprising one or more DNA sequences of the present invention. Preferably, the cloning or expression vector comprises two DNA sequences, encoding the light chain and the heavy chain of the antibody molecule of the present invention, respectively.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

DNA sequences which encode the antibody molecule of the present invention can be obtained by methods well known to those skilled in the art. For example, DNA sequences coding for part or all of the antibody heavy and light chains may be synthesised as desired from the determined DNA sequences or on the basis of the corresponding amino acid sequences.

DNA coding for acceptor framework sequences is widely available to those skilled in the art and can be readily synthesised on the basis of their known amino acid sequences.

Standard techniques of molecular biology may be used to prepare DNA sequences coding for the antibody molecule of the present invention. Desired DNA sequences may be synthesised completely or in part using oligonucleotide synthesis techniques. Site-directed mutagenesis and polymerase chain reaction (PCR) techniques may be used as appropriate.

Any suitable host cell/vector system may be used for expression of the DNA sequences encoding the antibody molecule of the present invention. Bacterial, for example *E. coli*, and other microbial systems may be used, in part, for expression of antibody fragments such as Fab and F(ab')$_2$ fragments, and especially Fv fragments and single chain antibody fragments, for example, single chain Fvs. Eukaryotic, e.g. mammalian, host cell expression systems may be used for production of larger antibody molecules, including complete antibody molecules. Suitable mammalian host cells include CHO, myeloma or hybridoma cells.

The present invention also provides a process for the production of an antibody molecule according to the present invention comprising culturing a host cell containing a vector of the present invention under conditions suitable for leading to expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

The present invention also provides a therapeutic or diagnostic composition comprising an antibody molecule of the present invention in combination with a pharmaceutically acceptable excipient, diluent or carrier.

The present invention also provides a process for preparation of a therapeutic or diagnostic composition comprising admixing the antibody molecule of the present invention together with a pharmaceutically acceptable excipient, diluent or carrier.

The antibody molecule may be the sole active ingredient in the therapeutic or diagnostic composition or may be accompanied by other active ingredients including other antibody ingredients, for example anti-T cell, anti-IFNγ or anti-LPS antibodies, or non-antibody ingredients such as xanthines.

The pharmaceutical compositions preferably comprise a therapeutically effective amount of the antibody of the invention. The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective dose can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, an effective dose will be from 0.01 mg/kg to 50 mg/kg, preferably 0.1 mg/kg to 20 mg/kg, more preferably about 15 mg/kg.

Compositions may be administered individually to a patient or may be administered in combination with other agents, drugs or hormones.

The dose at which the antibody molecule of the present invention is administered depends on the nature of the condition to be treated, the grade of the malignant lymphoma or leukaemia and on whether the antibody molecule is being used prophylactically or to treat an existing condition.

The frequency of dose will depend on the half-life of the antibody molecule and the duration of its effect. If the antibody molecule has a short half-life (e.g. 2 to 10 hours) it may be necessary to give one or more doses per day. Alternatively, if the antibody molecule has a long half life (e.g. 2 to 15 days) it may only be necessary to give a dosage once per day, once per week or even once every 1 or 2 months.

A pharmaceutical composition may also contain a pharmaceutically acceptable carrier for administration of the antibody. The carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Preferred forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject. The subjects to be treated can be animals. However, it is preferred that the compositions are adapted for administration to human subjects.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

It is also envisaged that the antibody of the present invention will be administered by use of gene therapy. In order to achieve this, DNA sequences encoding the heavy and light chains of the antibody molecule under the control of appropriate DNA components are introduced into a patient such that the antibody chains are expressed from the DNA sequences and assembled in situ.

The present invention also provides the antibody molecule of the present invention for use in treating a disease mediated by cells expressing CD22.

The present invention further provides the use of the antibody molecule according to the present invention in the manufacture of a medicament for the treatment of a disease mediated by cells expressing CD22.

The antibody molecule of the present invention may be utilised in any therapy where it is desired to reduce the level of cells expressing CD22 that are present in the human or animal body. These CD22-expressing cells may be circulating in the body or be present in an undesirably high level localised at a particular site in the body. For example, elevated levels of cells expressing CD22 will be present in B cell lymphomas and leukaemias. The antibody molecule of the present invention may be utilised in the therapy of diseases mediated by cells expressing CD22.

The antibody molecule of the present invention is preferably used for treatment of malignant lymphomas and leukaemias, most preferably NHL.

The present invention also provides a method of treating human or animal subjects suffering from or at risk of a disorder mediated by cells expressing CD22, the method comprising administering to the subject an effective amount of the antibody molecule of the present invention.

The antibody molecule of the present invention may also be used in diagnosis, for example in the in vivo diagnosis and imaging of disease states involving cells that express CD22.

The present invention is further described by way of illustration only in the following examples, which refer to the accompanying Figures, in which:

FIG. 1 shows the amino acid sequence of the CDRs of mouse monoclonal antibody 5/44 (SEQ ID NOS:1 to 6);

FIG. 2 shows the complete sequence of the light chain variable domain of mouse monoclonal antibody 5/44;

FIG. 3 shows the complete sequence of the heavy chain variable domain of mouse monoclonal antibody 5/44;

FIG. 4 shows the strategy for removal of the glycosylation site and reactive lysine in CDR-H2;

FIG. 5 shows the graft design for the 5/44 light chain sequence;

FIG. 6 shows the graft design for the 5/44 heavy chain sequence;

FIG. 7 shows the vectors pMRR14 and pMRR10.1;

FIG. 8 shows the Biacore assay results of the chimeric 5/44 mutants;

FIG. 9 shows the oligonucleotides for 5/44 gH1 and gL1 gene assemblies;

FIG. 10 shows the intermediate vectors pCR2.1(544gH1) and pCR2.1(544gL1);

FIG. 11 shows the oligonucleotide cassettes used to make further grafts;

FIG. 12 shows the competition assay between fluorescently labelled mouse 5/44 antibody and grafted variants; and FIG. 13 shows the full DNA and protein sequence of the grafted heavy and light chains.

DETAILED DESCRIPTION OF THE INVENTION

EXAMPLE 1

Generation of Candidate Antibodies

A panel of antibodies against CD22 were selected from hybridomas using the following selection criteria: binding to Daudi cells, internalisation on Daudi cells, binding to peripheral blood mononuclear cells (PBMC), internalisation on PBMC, affinity (greater than $10^{-9}M$), mouse γ1 and production rate. 5/44 was selected as the preferred antibody.

EXAMPLE 2

Gene Cloning and Expression of a Chimeric 5/44 Antibody Molecule

Preparation of 5/44 Hybridoma Cells and RNA Preparation therefrom

Hybridoma 5/44 was generated by conventional hybridoma technology following immunisation of mice with human CD22 protein. RNA was prepared from 5/44 hybridoma cells using a RNEasy kit (Qiagen, Crawley, UK; Catalogue No. 74106). The RNA obtained was reverse transcribed to cDNA, as described below.

Distribution of CD22 on NHL Tumours

An immunohistochemistry study was undertaken to examine the incidence and distribution of staining using the 5/44 anti-CD22 monoclonal antibodies. Control anti-CD20 and anti-CD79a antibodies were included in the study to confirm B cell areas of tumours.

A total of 50 tumours were studied and these were categorised as follows by using the Working Formulation and REAL classification systems:

7 B lymphoblastic leukaemia/lymphoma (High/l)
4 B-CLL/small lymphocytic lymphoma (Low/A)
3 lymphoplasmacytoid/Immunocytoma (Low/A)
1 Mantle cell (Int/F)
14 Follicle center lymphoma (Low to Int/D)
13 Diffuse large cell lymphoma (Int to High/G,H)
6 Unclassifiable (K)
2 T cell lymphomas 40 B cell lymphomas were positive for CD22 antigen with the 5/44 antibody at 0.1 µg/ml and a further 6 became positive when the concentration was increased to 0.5 µg/ml. For the remaining 2 B cell tumours that were negative at 0.1 µg/ml, there was insufficient tissue remaining to test at the higher concentration. However, parallel testing with another Celltech anti-CD22 antibody 6/13, which gave stronger staining than 5/44, resulted in all 48 B cell lymphomas staining positive for CD22.

Thus, it is possible to conclude that the CD22 antigen is widely expressed on B cell lymphomas and thus provides a suitable target for immunotherapy in NHL.

PCR Cloning of 5/44 $V_H$ and $V_L$ cDNA sequences coding for the variable domains of 5/44 heavy and light chains were synthesised using reverse transcriptase to produce single stranded cDNA copies of the mRNA present in the total RNA. This was then used as the template for amplification of the murine V-region sequences using specific oligonucleotide primers by the Polymerase Chain Reaction (PCR).

a) cDNA Synthesis cDNA was synthesised in a 20 µl reaction volume containing the following reagents: 50 mM Tris-HCl pH 8.3, 75 mM KCl, 10 mM dithiothreitol, 3 mM $MgCl_2$, 0.5 mM each deoxyribonucleoside triphosphate, 20 units RNAsin, 75 ng random hexanucleotide primer, 2 µg 5/44 RNA and 200 units Moloney Murine Leukemia Virus reverse transcriptase. After incubation at 42° C. for 60 minutes, the reaction was terminated by heating at 95° C. for 5 minutes.

b) PCR

Aliquots of the cDNA were subjected to PCR using combinations of primers specific for the heavy and light chains. Degenerate primer pools designed to anneal with the conserved sequences of the signal peptide were used as forward primers. These sequences all contain, in order, a restriction site ($V_L$ SfuI; $V_H$ HindIII) starting 7 nucleotides from their 5' ends, the sequence GCCGCCACC (SEQ ID NO:50), to allow optimal translation of the resulting mRNAs, an initiation codon and 20-30 nucleotides based on the leader peptide sequences of known mouse antibodies (Kabat et al., Sequences of proteins of immunological interest, 5$^{th}$ Edition, 1991, U.S. Department of Health and Human Services, Public Health Service, National Institutes of Health).

The 3' primers are designed to span the framework 4 J-C junction of the antibody and contain a restriction site for the enzyme BsiWI to facilitate cloning of the $V_L$ PCR fragment. The heavy chain 3' primers are a mixture designed to span the J-C junction of the antibody. The 3' primer includes an ApaI restriction site to facilitate cloning. The 3' region of the primers contains a mixed sequence based on those found in known mouse antibodies (Kabat et al., 1991, supra).

The combinations of primers described above enable the PCR products for $V_H$ and Vl to be cloned directly into an appropriate expression vector (see below) to produce chimeric (mouse-human) heavy and light chains and for these genes to be expressed in mammalian cells to produce chimeric antibodies of the desired isotype.

Incubations (100 µl) for the PCR were set up as follows. Each reaction contained 10 mM Tris-HCl pH 8.3, 1.5 mM $MgCl_2$, 50 mM KCl, 0.01% w/v gelatin, 0.25 mM each deoxyribonucleoside triphosphate, 10 pmoles 5' primer mix, 10 pmoles 3' primer, 1 µl cDNA and 1 unit Taq polymerase. Reactions were incubated at 95° C. for 5 minutes and then cycled through 94° C. for 1 minute, 55° C. for 1 minute and 72° C. for 1 minute. After 30 cycles, aliquots of each reaction were analysed by electrophoresis on an agarose gel.

For the heavy chain V-region, an amplified DNA product was only obtained when a primer pool annealing within the start of framework I replaced the signal peptide primer pool. The fragments were cloned into DNA sequencing vectors.

The DNA sequence was determined and translated to give a deduced amino acid sequence. This deduced sequence was verified by reference to the N-terminal protein sequence determined experimentally. FIGS. 2 and 3 shows the DNA/protein sequence of the mature light and heavy chain V-regions of mouse monoclonal 5/44 respectively.

c) Molecular Cloning of the PCR Fragments

The murine v-region sequences were then cloned into the expression vectors pMRR10.1 and pMRR14 (FIG. 7). These are vectors for the expression of light and heavy chain respectively containing DNA encoding constant regions of human kappa light chain and human gamma-4 heavy chain. The $V_L$ region was sub-cloned into the expression vector by restriction digest and ligation from the sequencing vector, using SfuI and BsiWI restriction sites, creating plasmid pMRR10(544cL). The heavy chain DNA was amplified by PCR using a 5' primer to introduce a signal peptide, since this was not obtained in the cloning strategy—a mouse heavy chain antibody leader from a different in-house hybridoma (termed 162) was employed. The 5' primer had the following sequence: 5'GCGCGCAAGCTTGCCGCCAC-CATGGACTTCGGATTCTCTCTCGTGTTC-CTGGCACTCATTCTCAAGGGAGTGCAGT-GTGAGGTGCAGCTCGTCGAGTCTGG3' (SEQ ID NO:51).

The reverse primer was identical to that used in the original $V_H$ gene cloning. The resultant PCR product was digested with enzymes HindIII and ApaI, was sub-cloned, and its DNA sequence was confirmed, creating plasmid pMRR14(544cH). Transient co-transfection of both expression vectors into CHO cells generated chimeric c5/44 antibody. This was achieved using the Lipofectamine reagent according to the manufacturer's protocols (InVitrogen:Life Technology, Groningen, The Netherlands. Catalogue no. 11668-027).

Removal of Glycosylation Site and Reactive Lysine

A potential N-linked glycosylation site sequence was observed in CDR-H2, having the amino acid sequence N-Y-T (FIG. 3). SDS-PAGE, Western blotting and carbohydrate staining of gels of 5/44 and its fragments (including Fab) indicated that this site was indeed glycosylated (not shown). In addition, a lysine residue was observed at an exposed position within CDR-H2, which had the potential to reduce the binding affinity of the antibody by providing an additional site for conjugation with an agent with which the antibody may be conjugated.

A PCR strategy was used to introduce amino acid substitutions into the CDR-H2 sequence in an attempt to remove the glycosylation site and/or the reactive lysine, as shown in FIG. 4. Forward primers encoding the mutations N55Q, T57A or T57V were used to remove the glycosylation site (FIG. 4) and a fourth forward primer containing the substitution K60R, was generated to remove the reactive lysine residue (FIG. 4). A framework 4 reverse primer was used in each of these PCR amplifications. The PCR products were digested with the enzymes XbaI and ApaI and were inserted into pMRR14(544cH) (also cleaved with XbaI and ApaI) to generate expression plasmids encoding these mutants. The N55Q, T57A and T57V mutations ablate the glycosylation site by changing the amino acid sequence away from the consensus N-X-T/S whilst the K60R mutation replaces the potentially reactive lysine with the similarly positively charged residue arginine. The resultant cH variant plasmids were co-transfected with the cL plasmid to generate expressed chimeric antibody variants.

Evaluation of Activities of Chimeric Genes

The activities of the chimeric genes were evaluated following transient transfection into CHO cells.

c) Determination of Affinity Constants by BiaCore Analysis.

The affinities of chimeric 5/44 or its variants, which have had their glycosylation site or their reactive lysine removed, were investigated using BIA technology for binding to CD22-mFc constructs. The results are shown in FIG. 8. All binding measurements were performed in the BIAcore™ 2000 instrument (Pharmacia Biosensor AB, Uppsala, Sweden). The assay was performed by capture of CD22mFc via the immobilised anti-mouse Fc. The antibody was in the soluble phase. Samples, standard, and controls (50 ul) were injected over immobilised anti-mouse Fc followed by antibody in the soluble phase. After each cycle the surface was regenerated with 50 ul of 40 mM HCl at 30 ul/min. The kinetic analysis was performed using the BIAevaluation 3.1 software (Pharmacia).

Removal of the glycosylation site in construct T57A resulted in a slightly faster on-rate and a significantly slower off-rate compared to the chimeric 5/44, giving an affinity improvement of approximately 5-fold. The N55Q mutation had no effect on affinity. This result was unexpected as it suggests that the removal of the carbohydrate itself apparently has no effect on binding (as with the N55Q change). The improved affinity was observed only with the T57A change. One possible explanation is that, regardless of the presence of carbohydrate, the threonine at position 57 exerts a negative effect on binding that is removed on conversion of threonine to alanine. The hypothesis that the small size of alanine is important, and that the negative effect of threonine is related to its size, is supported from the result obtained using the T57V mutation: that replacement with valine at position 57 is not beneficial (results not shown).

Removal of the lysine by the K60R mutation had a neutral effect on affinity, i.e. the introduction of arginine removes a potential reactive site without compromising affinity.

The mutations for removal of the glycosylation site and for removal of the reactive lysine were therefore both included in the humanisation design.

EXAMPLE 2

CDR-Grafting of 5/44

The molecular cloning of genes for the variable regions of the heavy and light chains of the 5/44 antibody and their use to produce chimeric (mouse/human) 5/44 antibodies has been described above. The nucleotide and amino acid sequences of the mouse 5/44 $V_L$ and $V_H$ domains are shown in FIGS. 2 and 3 (SEQ ID NOS:7 and 8), respectively. This example describes the CDR-grafting of the 5/44 antibody onto human frameworks to reduce potential immunogenicity in humans, according to the method of Adair et al., (WO91/09967).

CDR-Grafting of 5/44 Light Chain

Protein sequence alignment with consensus sequences from human sub-group I kappa light chain V region indicated 64% sequence identity. Consequently, for constructing the CDR-grafted light chain, the acceptor framework regions chosen corresponded to those of the human VK sub-group I germline O12,DPK9 sequence. The framework 4 acceptor sequence was derived from the human J-region germline sequence JK1.

A comparison of the amino acid sequences of the framework regions of murine 5/44 and the acceptor sequence is given in FIG. 5 and shows that there are 27 differences between the donor and acceptor chains. At each position, an analysis was made of the potential of the murine residue to contribute to antigen binding, either directly or indirectly, through effects on packing or at the $V_H/V_L$ interface. If a murine residue was considered important and sufficiently different from the human residue in terms of size, polarity or charge, then that murine residue was retained. Based on this analysis, two versions of the CDR-grafted light chain, having the sequences given in SEQ ID NO:19 and SEQ ID NO:20 (FIG. 5), were constructed.

CDR-Grafting of 5/44 Heavy Chain

CDR-grafting of 5/44 heavy chain was accomplished using the same strategy as described for the light chain. The V-domain of 5/44 heavy chain was found to be homologous to human heavy chains belonging to sub-group I (70% sequence identity) and therefore the sequence of the human sub-group I germline framework VH1-3,DP7 was used as an acceptor framework. The framework 4 acceptor sequences were derived from human J-region germline sequence JH4.

A comparison of 5/44 heavy chain with the framework regions is shown in FIG. 6 where it can be seen that the 5/44 heavy chain differs from the acceptor sequence at 22 positions. Analysis of the contribution that any of these might make to antigen binding led to 5 versions of the CDR-grafted heavy chains being constructed, having the sequences given in SEQ ID NO:23, SEQ ID NO:24, SEQ ID NO:25, SEQ ID NO:26 and SEQ ID NO:27 (FIG. 6).

Construction of Genes for Grafted Sequences.

Genes were designed to encode the grafted sequences gH1 and gL1, and a series of overlapping oligonucleotides were designed and constructed (FIG. 9). A PCR assembly technique was employed to construct the CDR-grafted V-region genes. Reaction volumes of 100 ul were set up containing 10 mM Tris-HCl pH8.3, 1.5 mM MgCl2, 50 mM KCl, 0.001% gelatin, 0.25 mM each deoxyribonucleoside triphosphate, 1 pmole each of the 'internal' primers (T1, T2, T3, B1, B2, B3), 10 pmole each of the 'external' primers (F1, R1), and 1 unit of Taq polymerase (AmpliTaq, Applied BioSystems, catalogue no. N808-0171). PCR cycle parameters were 94° C. for 1 minute, 55° C. for 1 minute and 72° C. for 1 minute, for 30 cycles. The reaction products were then run on a 1.5% agarose gel, excised and recovered using QIAGEN spin columns (QIAquick gel extraction kit, cat no. 28706). The DNA was eluted in a volume of 30 µl. Aliquots (1 µl) of the gH1 and gL1 DNA were then cloned into the InVitrogen TOPO TA cloning vector pCR2.1 TOPO (catalogue no. K4500-01) according to the manufacturer's instructions. This non-expression vector served as a cloning intermediate to facilitate sequencing of a large number of clones. DNA sequencing using vector-specific primers was used to identify correct clones containing gH1 and gL1, creating plasmids pCR2.1 (544gH1) and pCR2.1(544gL1) (FIG. 10).

An oligonucleotide cassette replacement method was used to create the humanised grafts gH4,5,6 and 7, and gL2. FIG. 11 shows the design of the oligonucleotide cassettes. To construct each variant, the vector (pCR2.1(544gH1) or pCR2.1(544gL1)) was cut with the restriction enzymes shown (XmaI/SacII for the heavy chain, XmaI/BstEII for the light chain). The large vector fragment was gel purified from agarose and was used in ligation with the oligonucleotide cassette. These cassettes are composed of 2 complementary oligonucleotides (shown in FIG. 11), mixed at a concentration of 0.5 pmoles/µl in a volume of 200 µl 12.5 mM Tris-HCl pH 7.5, 2.5 mM MgCl$_2$, 25 mM NaCl, 0.25 mM dithioerythritol. Annealing was achieved by heating to 95° C. for 3 minutes in a waterbath (volume 500 ml) then allowing the reaction to slow-cool to room temperature. The annealed oligonucleotide cassette was then diluted ten-fold in water before ligation into the appropriately cut vector. DNA sequencing was used to confirm the correct sequence, creating plasmids pCR2.1 (5/44-gH4-7) and pCR2.1(5/44-gL2). The verified grafted sequences were then sub-cloned into the expression vectors pMRR14 (heavy chain) and pMR10.1 (light chain).

CD22 Binding Activity of CDR-grafted Sequences

The vectors encoding grafted variants were co-transfected into CHO cells in a variety of combinations, together with the original chimeric antibody chains. Binding activity was compared in a competition assay, competing the binding of the original mouse 5/44 antibody for binding to Ramos cells (obtained from ATCC, a Burkitt's lymphoma lymphoblast human cell line expressing surface CD22). This assay was considered the best way to compare grafts in their ability to bind to cell surface CD22. The results are shown in FIG. 8. As can be seen, there is very little difference between any of the grafts, all performing more effectively than the chimeric at competing against the murine parent. The introduction of the 3 additional human residues at the end of CDR-H3 (gH5 and gH7) does not appear to have affected binding.

The graft combination with the least number of murine residues was selected, gL1gH7. The light chain graft gL1 has 6 donor residues. Residues V2, V4, L37 and Q45 are potentially important packing residues. Residue H38 is at the $V_H/V_L$ interface. Residue D60 is a surface residue close to the CDR-L2 and may directly contribute to antigen binding. Of these residues, V2, L37, Q45 and D60 are found in germline sequences of human kappa genes from other sub-groups. The heavy chain graft gH7 has 4 donor framework residues (Residue R28 is considered to be part of CDR-H1 under the structural definition used in CDR-grafting (se Adair et al (1991 WO91/09967)). Residues E1 and A71 are surface residues close to the CDR's. Residue I48 is a potential packing residue. Residue T93 is present at the $V_H/V_L$ interface. Of these residues, E1 and A71 are found in other germline genes of human sub-group I. Residue I48 is found in human germline sub-group 4, and T73 is found in human germline sub-group 3.

The full DNA and protein sequence of both the light chain and heavy chain, including approximate position of introns within the constant region genes provided by the vectors, are shown in FIG. 13 and are given in SEQ ID NO:29 and SEQ ID NO:28 respectively for the light chain and SEQ ID NO: 31 and SEQ ID NO:30 respectively for the heavy chain.

DNA encoding these light and heavy chain genes was excised from these vectors. Heavy chain DNA was digested at the 5' HindIII site, then was treated with the Klenow fragment of *E. coli* DNA polymerase I to create a 5' blunt end. Cleavage at the 3' EcoRI site resulted in the heavy chain fragment which was purified from agarose gels. In the same way, a light chain frament was produced, blunted at the 5' SfuI site and with a 3' EcoRI site. Both fragments were cloned into DHFR based expression vectors and used to generate stable cell lines in CHO cells.

All references and patents cited herein are hereby incorporated by reference in their entireties.

What is claimed is:

1. An antibody molecule consisting essentially of antibody domains, said antibody molecule having specificity for human CD22, comprising the light chain variable region 5/44-gL1 (SEQ ID NO:19) and the heavy chain variable region 5/44-gH7 (SEQ ID NO:27).

2. An antibody molecule consisting essentially of antibody domains, said antibody molecule having specificity for human CD22, having a light chain comprising the sequence given in SEQ ID NO:28 and a heavy chain comprising the sequence given in SEQ ID NO:30.

3. An antibody molecule consisting essentially of antibody domains, said antibody molecule having specificity for human CD22, having a light chain consisting of the sequence given in SEQ ID NO:28 and a heavy chain consisting of the sequence given in SEQ ID NO:30.

4. A murine anti-CD22 monoclonal antibody consisting essentially of antibody domains, wherein the variable domain of the light chain has the sequence given in SEQ ID NO: 7 and the variable domain of the heavy chain has the sequence given in SEQ ID NO: 8.

5. A chimeric antibody molecule consisting essentially of antibody domains, said antibody molecule comprising the sequences of the light and heavy chain variable domains of the monoclonal antibody of claim 4, recited in SEQ ID NO:7 and SEQ ID NO:8 respectively.

* * * * *

SEQUENCE LISTING

<160> NUMBER OF SEQ ID NOS: 51

<210> SEQ ID NO 1
<211> LENGTH: 5
<212> TYPE: PRT
<213> ORGANISM: mouse
<220> FEATURE:
<221> NAME/KEY: DOMAIN
<223> OTHER INFORMATION: mouse monoclonal 5/44 CDR-H1

<400> SEQUENCE: 1

Asn Tyr Trp Ile His
1               5

<210> SEQ ID NO 2
<211> LENGTH: 17
<212> TYPE: PRT
<213> ORGANISM: mouse
<220> FEATURE:
<221> NAME/KEY: DOMAIN
<223> OTHER INFORMATION: mouse monoclonal 5/44 CDR-H2

<400> SEQUENCE: 2

Gly Ile Asn Pro Gly Asn Asn Tyr Thr Thr Tyr Lys Arg Asn Leu Lys
1               5                   10                  15

Gly

<210> SEQ ID NO 3
<211> LENGTH: 12
<212> TYPE: PRT
<213> ORGANISM: mouse
<220> FEATURE:
<221> NAME/KEY: DOMAIN
<223> OTHER INFORMATION: mouse monoclonal 5/44 CDR-H3

<400> SEQUENCE: 3

Glu Gly Tyr Gly Asn Tyr Gly Ala Trp Phe Ala Tyr
1               5                   10

<210> SEQ ID NO 4
<211> LENGTH: 16
<212> TYPE: PRT
<213> ORGANISM: mouse
<220> FEATURE:
<221> NAME/KEY: DOMAIN
<223> OTHER INFORMATION: mouse monoclonal 5/44 CDR-L1

<400> SEQUENCE: 4

Arg Ser Ser Gln Ser Leu Ala Asn Ser Tyr Gly Asn Thr Phe Leu Ser
1               5                   10                  15

<210> SEQ ID NO 5
<211> LENGTH: 7
<212> TYPE: PRT
<213> ORGANISM: mouse
<220> FEATURE:
<221> NAME/KEY: DOMAIN
<223> OTHER INFORMATION: mouse monoclonal 5/44 CDR-L2

<400> SEQUENCE: 5

Gly Ile Ser Asn Arg Phe Ser
1               5

<210> SEQ ID NO 6
<211> LENGTH: 9

-continued

```
<212> TYPE: PRT
<213> ORGANISM: mouse
<220> FEATURE:
<221> NAME/KEY: DOMAIN
<223> OTHER INFORMATION: mouse monoclonal 5/44 CDR-L3

<400> SEQUENCE: 6

Leu Gln Gly Thr His Gln Pro Tyr Thr
1               5

<210> SEQ ID NO 7
<211> LENGTH: 113
<212> TYPE: PRT
<213> ORGANISM: mouse
<220> FEATURE:
<221> NAME/KEY: DOMAIN
<223> OTHER INFORMATION: mouse monoclonal 5/44 VL domain

<400> SEQUENCE: 7

Asp Val Val Thr Gln Thr Pro Leu Ser Leu Pro Val Ser Phe Gly
1               5                   10                  15

Asp Gln Val Ser Ile Ser Cys Arg Ser Ser Gln Ser Leu Ala Asn Ser
                20                  25                  30

Tyr Gly Asn Thr Phe Leu Ser Trp Tyr Leu His Lys Pro Gly Gln Ser
            35                  40                  45

Pro Gln Leu Leu Ile Tyr Gly Ile Ser Asn Arg Phe Ser Gly Val Pro
    50                  55                  60

Asp Arg Phe Thr Gly Ser Gly Ser Gly Thr Asp Phe Thr Leu Lys Ile
65                  70                  75                  80

Ser Thr Ile Lys Pro Glu Asp Leu Gly Met Tyr Tyr Cys Leu Gln Gly
                85                  90                  95

Thr His Gln Pro Tyr Thr Phe Gly Gly Gly Thr Lys Leu Glu Ile Lys
            100                 105                 110

Arg

<210> SEQ ID NO 8
<211> LENGTH: 121
<212> TYPE: PRT
<213> ORGANISM: mouse
<220> FEATURE:
<221> NAME/KEY: DOMAIN
<223> OTHER INFORMATION: mouse monoclonal 5/44 VH domain

<400> SEQUENCE: 8

Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Arg Phe Thr Asn Tyr
                20                  25                  30

Trp Ile His Trp Val Lys Gln Arg Pro Gly Gln Gly Leu Glu Trp Ile
            35                  40                  45

Gly Gly Ile Asn Pro Gly Asn Asn Tyr Thr Thr Tyr Lys Arg Asn Leu
    50                  55                  60

Lys Gly Lys Ala Thr Leu Thr Ala Val Thr Ser Ala Ser Thr Ala Tyr
65                  70                  75                  80

Met Asp Leu Ser Ser Leu Thr Ser Glu Asp Ser Ala Val Tyr Tyr Cys
                85                  90                  95

Thr Arg Glu Gly Tyr Gly Asn Tyr Gly Ala Trp Phe Ala Tyr Trp Gly
            100                 105                 110

Gln Gly Thr Leu Val Thr Val Ser Ser
            115                 120
```

<210> SEQ ID NO 9
<211> LENGTH: 13
<212> TYPE: PRT
<213> ORGANISM: Artificial Sequence
<220> FEATURE:
<221> NAME/KEY: DOMAIN
<223> OTHER INFORMATION: cH

<400> SEQUENCE: 9

Gly Asn Asn Tyr Thr Thr Tyr Lys Arg Asn Leu Lys Gly
1               5                   10

<210> SEQ ID NO 10
<211> LENGTH: 13
<212> TYPE: PRT
<213> ORGANISM: Artificial Sequence
<220> FEATURE:
<221> NAME/KEY: DOMAIN
<223> OTHER INFORMATION: CDR-H2 MUTATION N55Q

<400> SEQUENCE: 10

Gly Asn Gln Tyr Thr Thr Tyr Lys Arg Asn Leu Lys Gly
1               5                   10

<210> SEQ ID NO 11
<211> LENGTH: 13
<212> TYPE: PRT
<213> ORGANISM: Artificial Sequence
<220> FEATURE:
<221> NAME/KEY: DOMAIN
<223> OTHER INFORMATION: CDR-H2 MUTATION T57A

<400> SEQUENCE: 11

Gly Asn Asn Tyr Ala Thr Tyr Lys Arg Asn Leu Lys Gly
1               5                   10

<210> SEQ ID NO 12
<211> LENGTH: 13
<212> TYPE: PRT
<213> ORGANISM: Artificial Sequence
<220> FEATURE:
<221> NAME/KEY: DOMAIN
<223> OTHER INFORMATION: CDR-H2 MUTATION T57V

<400> SEQUENCE: 12

Gly Asn Asn Tyr Val Thr Tyr Lys Arg Asn Leu Lys Gly
1               5                   10

<210> SEQ ID NO 13
<211> LENGTH: 17
<212> TYPE: PRT
<213> ORGANISM: ARTIFICIAL SEQUENCE
<220> FEATURE:
<221> NAME/KEY: DOMAIN
<223> OTHER INFORMATION: CDR-H2 MUTATION (T57A) H'

<400> SEQUENCE: 13

Gly Ile Asn Pro Gly Asn Asn Tyr Ala Thr Tyr Lys Arg Asn Leu Lys
1               5                   10                  15

Gly

<210> SEQ ID NO 14
<211> LENGTH: 13
<212> TYPE: PRT
<213> ORGANISM: Artificial Sequence
<220> FEATURE:

```
<221> NAME/KEY: DOMAIN
<223> OTHER INFORMATION: CDR-H2 MUTATION K60R

<400> SEQUENCE: 14

Gly Asn Asn Tyr Thr Thr Tyr Arg Arg Asn Leu Lys Gly
1               5                   10

<210> SEQ ID NO 15
<211> LENGTH: 17
<212> TYPE: PRT
<213> ORGANISM: ARTIFICIAL SEQUENCE
<220> FEATURE:
<221> NAME/KEY: DOMAIN
<223> OTHER INFORMATION: CDR-H2 MUTATION (K60R) H''

<400> SEQUENCE: 15

Gly Ile Asn Pro Gly Asn Asn Tyr Thr Thr Tyr Arg Arg Asn Leu Lys
1               5                   10                  15

Gly

<210> SEQ ID NO 16
<211> LENGTH: 17
<212> TYPE: PRT
<213> ORGANISM: ARTIFICIAL SEQUENCE
<220> FEATURE:
<221> NAME/KEY: DOMAIN
<223> OTHER INFORMATION: CDR-H2 MUTATION (T57A K60R) H'''

<400> SEQUENCE: 16

Gly Ile Asn Pro Gly Asn Asn Tyr Ala Thr Tyr Arg Arg Asn Leu Lys
1               5                   10                  15

Gly

<210> SEQ ID NO 17
<211> LENGTH: 70
<212> TYPE: PRT
<213> ORGANISM: Homo sapiens
<220> FEATURE:
<221> NAME/KEY: DOMAIN
<223> OTHER INFORMATION: DPK9 HUMAN ACCEPTOR FRAMEWORK

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Trp Tyr Gln Gln Lys Pro Gly Lys Ala
                20                  25                  30

Pro Lys Leu Leu Ile Tyr Gly Val Pro Ser Arg Phe Ser Gly Ser Gly
            35                  40                  45

Ser Gly Thr Asp Phe Thr Leu Thr Ile Ser Ser Leu Gln Pro Glu Asp
        50                  55                  60

Phe Ala Thr Tyr Tyr Cys
65                  70

<210> SEQ ID NO 18
<211> LENGTH: 11
<212> TYPE: PRT
<213> ORGANISM: Homo sapiens
<220> FEATURE:
<221> NAME/KEY: DOMAIN
<223> OTHER INFORMATION: JK1 HUMAN ACCEPTOR FRAMEWORK

<400> SEQUENCE: 18

Phe Gly Gln Gly Thr Lys Val Glu Ile Lys Arg
1               5                   10
```

<210> SEQ ID NO 19
<211> LENGTH: 113
<212> TYPE: PRT
<213> ORGANISM: Artificial Sequence
<220> FEATURE:
<221> NAME/KEY: CHAIN
<223> OTHER INFORMATION: gL1

<400> SEQUENCE: 19

Asp Val Gln Val Thr Gln Ser Pro Ser Ser Leu Ser Ala Ser Val Gly
1               5                   10                  15

Asp Arg Val Thr Ile Thr Cys Arg Ser Ser Gln Ser Leu Ala Asn Ser
            20                  25                  30

Tyr Gly Asn Thr Phe Leu Ser Trp Tyr Leu His Lys Pro Gly Lys Ala
        35                  40                  45

Pro Gln Leu Leu Ile Tyr Gly Ile Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Leu Gln Gly
                85                  90                  95

Thr His Gln Pro Tyr Thr Phe Gly Gln Gly Thr Lys Val Glu Ile Lys
            100                 105                 110

Arg

<210> SEQ ID NO 20
<211> LENGTH: 113
<212> TYPE: PRT
<213> ORGANISM: Artificial Sequence
<220> FEATURE:
<221> NAME/KEY: CHAIN
<223> OTHER INFORMATION: gL2

<400> SEQUENCE: 20

Asp Val Val Val Thr Gln Ser Pro Ser Ser Leu Ser Ala Ser Val Gly
1               5                   10                  15

Asp Arg Val Thr Ile Thr Cys Arg Ser Ser Gln Ser Leu Ala Asn Ser
            20                  25                  30

Tyr Gly Asn Thr Phe Leu Ser Trp Tyr Leu His Lys Pro Gly Lys Ala
        35                  40                  45

Pro Gln Leu Leu Ile Tyr Gly Ile Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Leu Gln Gly
                85                  90                  95

Thr His Gln Pro Tyr Thr Phe Gly Gln Gly Thr Lys Val Glu Ile Lys
            100                 105                 110

Arg

<210> SEQ ID NO 21
<211> LENGTH: 80
<212> TYPE: PRT
<213> ORGANISM: Homo sapiens
<220> FEATURE:
<221> NAME/KEY: CHAIN
<223> OTHER INFORMATION: DP7 HUMAN ACCEPTOR FRAMEWORK

<400> SEQUENCE: 21

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Trp Val
            20                  25                  30

Arg Gln Ala Pro Gly Gln Gly Leu Glu Trp Met Gly Lys Phe Gln Gly
        35                  40                  45

Arg Val Thr Met Thr Arg Asp Thr Ser Thr Ser Thr Val Tyr Met Glu
    50                  55                  60

Leu Ser Ser Leu Arg Ser Glu Asp Thr Ala Val Tyr Tyr Cys Ala Arg
65                  70                  75                  80
```

<210> SEQ ID NO 22
<211> LENGTH: 11
<212> TYPE: PRT
<213> ORGANISM: Homo sapiens
<220> FEATURE:
<221> NAME/KEY: DOMAIN
<223> OTHER INFORMATION: JH4 HUMAN ACCEPTOR FRAMEWORK

<400> SEQUENCE: 22

```
Trp Gly Gln Gly Thr Leu Val Thr Val Ser Ser
1               5                   10
```

<210> SEQ ID NO 23
<211> LENGTH: 121
<212> TYPE: PRT
<213> ORGANISM: Artificial Sequence
<220> FEATURE:
<221> NAME/KEY: CHAIN
<223> OTHER INFORMATION: gH1

<400> SEQUENCE: 23

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Thr Asn Tyr
            20                  25                  30

Trp Ile His Trp Val Arg Gln Ala Pro Gly Gln Gly Leu Glu Trp Ile
        35                  40                  45

Gly Gly Ile Asn Pro Gly Asn Gln Tyr Thr Thr Tyr Lys Arg Asn Leu
    50                  55                  60

Lys Gly Arg Ala Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Glu Gly Tyr Gly Asn Tyr Gly Ala Trp Phe Ala Tyr Trp Gly
            100                 105                 110

Gln Gly Thr Leu Val Thr Val Ser Ser
        115                 120
```

<210> SEQ ID NO 24
<211> LENGTH: 121
<212> TYPE: PRT
<213> ORGANISM: Artificial Sequence
<220> FEATURE:
<221> NAME/KEY: CHAIN
<223> OTHER INFORMATION: gH4

<400> SEQUENCE: 24

```
Glu Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Arg Phe Thr Asn Tyr
            20                  25                  30

Trp Ile His Trp Val Arg Gln Ala Pro Gly Gln Gly Leu Glu Trp Ile
        35                  40                  45

Gly Gly Ile Asn Pro Gly Asn Asn Tyr Ala Thr Tyr Arg Arg Asn Leu
    50                  55                  60

Lys Gly Arg Ala Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Glu Gly Tyr Gly Asn Tyr Gly Ala Trp Phe Ala Tyr Trp Gly
            100                 105                 110

Gln Gly Thr Leu Val Thr Val Ser Ser
            115                 120

<210> SEQ ID NO 25
<211> LENGTH: 121
<212> TYPE: PRT
<213> ORGANISM: Artificial Sequence
<220> FEATURE:
<221> NAME/KEY: CHAIN
<223> OTHER INFORMATION: gH5

<400> SEQUENCE: 25

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Thr Asn Tyr
            20                  25                  30

Trp Ile His Trp Val Arg Gln Ala Pro Gly Gln Gly Leu Glu Trp Ile
        35                  40                  45

Gly Gly Ile Asn Pro Gly Asn Asn Tyr Ala Thr Tyr Arg Arg Asn Leu
    50                  55                  60

Lys Gly Arg Val Thr Met Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Glu Gly Tyr Gly Asn Tyr Gly Ala Trp Phe Ala Tyr Trp Gly
            100                 105                 110

Gln Gly Thr Leu Val Thr Val Ser Ser
            115                 120

<210> SEQ ID NO 26
<211> LENGTH: 121
<212> TYPE: PRT
<213> ORGANISM: Artificial Sequence
<220> FEATURE:
<221> NAME/KEY: CHAIN
<223> OTHER INFORMATION: gH6

<400> SEQUENCE: 26

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Thr Asn Tyr
            20                  25                  30

Trp Ile His Trp Val Arg Gln Ala Pro Gly Gln Gly Leu Glu Trp Ile
        35                  40                  45

Gly Gly Ile Asn Pro Gly Asn Asn Tyr Ala Thr Tyr Arg Arg Lys Phe
    50                  55                  60
```

```
Gln Gly Arg Ala Thr Leu Thr Ala Asp Thr Ser Ser Thr Val Tyr
 65                  70                  75                  80

Met Glu Leu Ser Ser Leu Arg Ser Glu Asp Thr Ala Val Tyr Tyr Cys
                 85                  90                  95

Thr Arg Glu Gly Tyr Gly Asn Tyr Gly Ala Trp Phe Ala Tyr Trp Gly
                100                 105                 110

Gln Gly Thr Leu Val Thr Val Ser Ser
            115                 120

<210> SEQ ID NO 27
<211> LENGTH: 121
<212> TYPE: PRT
<213> ORGANISM: Artificial Sequence
<220> FEATURE:
<221> NAME/KEY: CHAIN
<223> OTHER INFORMATION: gH7

<400> SEQUENCE: 27

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Arg Phe Thr Asn Tyr
                 20                  25                  30

Trp Ile His Trp Val Arg Gln Ala Pro Gly Gln Gly Leu Glu Trp Ile
             35                  40                  45

Gly Gly Ile Asn Pro Gly Asn Asn Tyr Ala Thr Tyr Arg Arg Lys Phe
         50                  55                  60

Gln Gly Arg Val Thr Met Thr Ala Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Thr Arg Glu Gly Tyr Gly Asn Tyr Gly Ala Trp Phe Ala Tyr Trp Gly
                100                 105                 110

Gln Gly Thr Leu Val Thr Val Ser Ser
            115                 120

<210> SEQ ID NO 28
<211> LENGTH: 239
<212> TYPE: PRT
<213> ORGANISM: Artificial Sequence
<220> FEATURE:
<221> NAME/KEY: CHAIN
<223> OTHER INFORMATION: Full sequence of grafted light chain

<400> SEQUENCE: 28

Met Lys Leu Pro Val Arg Leu Leu Val Leu Leu Phe Trp Ile Pro
 1               5                  10                  15

Ala Ser Arg Gly Asp Val Gln Val Thr Gln Ser Pro Ser Ser Leu Ser
                 20                  25                  30

Ala Ser Val Gly Asp Arg Val Thr Ile Thr Cys Arg Ser Ser Gln Ser
             35                  40                  45

Leu Ala Asn Ser Tyr Gly Asn Thr Phe Leu Ser Trp Tyr Leu His Lys
         50                  55                  60

Pro Gly Lys Ala Pro Gln Leu Leu Ile Tyr Gly Ile Ser Asn Arg Phe
 65                  70                  75                  80

Ser Gly Val Pro Asp Arg Phe Ser Gly Ser Gly Ser Gly Thr Asp Phe
                 85                  90                  95

Thr Leu Thr Ile Ser Ser Leu Gln Pro Glu Asp Phe Ala Thr Tyr Tyr
                100                 105                 110
```

-continued

```
Cys Leu Gln Gly Thr His Gln Pro Tyr Thr Phe Gly Gln Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

<210> SEQ ID NO 29
<211> LENGTH: 781
<212> TYPE: DNA
<213> ORGANISM: ARTIFICIAL
<220> FEATURE:
<221> NAME/KEY: CDS
<223> OTHER INFORMATION: Full DNA sequence of grafted light chain

<400> SEQUENCE: 29

```
ttcgaagccg ccaccatgaa gttgcctgtt aggctgttgg tgcttctgtt gttctggatt     60
cctgcttccc ggggtgacgt tcaagtgacc cagagcccat ccagcctgag cgcatctgta    120
ggagaccggg tcaccatcac ttgtagatcc agtcagagtc ttgcaaacag ttatgggaac    180
accttttgt cttggtatct gcacaaacca ggtaaagccc acaattgct catctacgga     240
atctctaaca gatttagtgg tgtaccagac aggttcagcg gttccggaag tggtactgat    300
ttcaccctca cgatctcgtc tctccagcca gaagatttcg ccacttatta ctgtttacaa    360
ggtacacatc agccgtacac attcggtcag ggtactaaag tagaaatcaa acgtacggta    420
gcggccccat ctgtcttcat cttcccgcca tctgatgagc agttgaaatc tggaactgcc    480
tctgttgtgt gcctgctgaa taacttctat cccagagagg ccaaagtaca gtggaaggtg    540
gataacgccc tccaatcggg taactcccag gagagtgtca cagagcagga cagcaaggac    600
agcacctaca gcctcagcag caccctgacg ctgagcaaag cagactacga gaaacacaaa    660
gtctacgcct gcgaagtcac ccatcagggc ctgagctcgc ccgtcacaaa gagcttcaac    720
aggggagagt gttagaggga gaagtgcccc cacctgctcc tcagttccag cctgggaatt    780
c                                                                   781
```

<210> SEQ ID NO 30
<211> LENGTH: 467
<212> TYPE: PRT
<213> ORGANISM: Artificial Sequence
<220> FEATURE:
<221> NAME/KEY: CHAIN
<223> OTHER INFORMATION: Full sequence of grafted heavy chain

<400> SEQUENCE: 30

```
Met Asp Phe Gly Phe Ser Leu Val Phe Leu Ala Leu Ile Leu Lys Gly
1               5                   10                  15

Val Gln Cys Glu Val Gln Leu Val Gln Ser Gly Ala Glu Val Lys Lys
            20                  25                  30
```

```
Pro Gly Ala Ser Val Lys Val Ser Cys Lys Ala Ser Gly Tyr Arg Phe
            35                  40                  45

Thr Asn Tyr Trp Ile His Trp Val Arg Gln Ala Pro Gly Gln Gly Leu
        50                  55                  60

Glu Trp Ile Gly Gly Ile Asn Pro Gly Asn Asn Tyr Ala Thr Tyr Arg
65                  70                  75                  80

Arg Lys Phe Gln Gly Arg Val Thr Met Thr Ala Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Thr Arg Glu Gly Tyr Gly Asn Tyr Gly Ala Trp Phe Ala
        115                 120                 125

Tyr Trp Gly Gln Gly Thr Leu Val Thr Val Ser Ser Ala Ser Thr Lys
130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Lys Thr Tyr Thr Cys Asn
210                 215                 220

Val Asp His Lys Pro Ser Asn Thr Lys Val Asp Lys Arg Val Glu Ser
225                 230                 235                 240

Lys Tyr Gly Pro Pro Cys Pro Pro Cys Pro Ala Pro Glu Phe Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser Gln
        275                 280                 285

Glu Asp Pro Glu Val Gln Phe Asn Trp Tyr Val Asp Gly Val Glu Val
290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Gln Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Arg Leu Thr Val
            420                 425                 430

Asp Lys Ser Arg Trp Gln Glu Gly Asn Val Phe Ser Cys Ser Val Met
        435                 440                 445
```

His Glu Ala Leu His Asn His Tyr Thr Gln Lys Ser Leu Ser Leu Ser
    450                 455                 460

Leu Gly Lys
465

<210> SEQ ID NO 31
<211> LENGTH: 2160
<212> TYPE: DNA
<213> ORGANISM: Artificial Sequence
<220> FEATURE:
<221> NAME/KEY: CDS
<223> OTHER INFORMATION: Full DNA sequence of grafted heavy chain

<400> SEQUENCE: 31

| | | | | |
|---|---|---|---|---|
| aagcttgccg | ccaccatgga | cttcggattc | tctctcgtgt | tcctggcact | cattctcaag |   60 |
| ggagtgcagt | gtgaggtgca | attggtccag | tcaggagcag | aggttaagaa | gcctggtgct |  120 |
| tccgtcaaag | tttcgtgtaa | ggctagcggc | tacaggttca | caaattattg | gattcattgg |  180 |
| gtcaggcagg | ctccgggaca | aggcctggaa | tggatcggtg | gcattaatcc | cgggaataac |  240 |
| tacgctacat | ataggagaaa | attccagggc | agagttacga | tgaccgcgga | cacctccaca |  300 |
| agcactgtct | acatggagct | gtcatctctg | agatccgagg | acaccgcagt | gtactattgt |  360 |
| actagagaag | gctacggtaa | ttacggagcc | tggttcgcct | actggggcca | gggtacccta |  420 |
| gtcacagtct | cctcagcttc | tacaaagggc | ccatccgtct | tccccctggc | gccctgctcc |  480 |
| aggagcacct | ccgagagcac | agccgccctg | ggctgcctgg | tcaaggacta | cttccccgaa |  540 |
| ccggtgacgg | tgtcgtggaa | ctcaggcgcc | ctgaccagcg | gcgtgcacac | cttcccggct |  600 |
| gtcctacagt | cctcaggact | ctactccctc | agcagcgtgg | tgaccgtgcc | ctccagcagc |  660 |
| ttgggcacga | agacctacac | ctgcaacgta | gatcacaagc | ccagcaacac | caaggtggac |  720 |
| aagagagttg | gtgagaggcc | agcacaggga | gggagggtgt | ctgctggaag | ccaggctcag |  780 |
| ccctcctgcc | tggacgcacc | ccggctgtgc | agccccagcc | cagggcagca | aggcatgccc |  840 |
| catctgtctc | ctcacccgga | ggcctctgac | caccccactc | atgcccaggg | agagggtctt |  900 |
| ctggattttt | ccaccaggct | ccgggcagcc | acaggctgga | tgcccctacc | ccaggccctg |  960 |
| cgcatacagg | ggcaggtgct | gcgctcagac | ctgccaagag | ccatatccgg | aggaccctg  | 1020 |
| cccctgacct | aagcccaccc | caaaggccaa | actctccact | ccctcagctc | agacaccttc | 1080 |
| tctcctccca | gatctgagta | actcccaatc | ttctctctgc | agagtccaaa | tatggtcccc | 1140 |
| catgcccacc | atgcccaggt | aagccaaccc | aggcctcgcc | ctccagctca | aggcgggaca | 1200 |
| ggtgccctag | agtagcctgc | atccagggac | aggccccagc | cgggtgctga | cgcatccacc | 1260 |
| tccatctctt | cctcagcacc | tgagttcctg | gggggaccat | cagtcttcct | gttcccccca | 1320 |
| aaacccaagg | acactctcat | gatctcccgg | acccctgagg | tcacgtgcgt | ggtggtggac | 1380 |
| gtgagccagg | aagaccccga | ggtccagttc | aactggtacg | tggatggcgt | ggaggtgcat | 1440 |
| aatgccaaga | caaagccgcg | ggaggagcag | ttcaacagca | cgtaccgtgt | ggtcagcgtc | 1500 |
| ctcaccgtcc | tgcaccagga | ctggctgaac | ggcaaggagt | acaagtgcaa | ggtctccaac | 1560 |
| aaaggcctcc | cgtcctccat | cgagaaaacc | atctccaaag | ccaaaggtgg | gacccacggg | 1620 |
| gtgcgagggc | cacatggaca | gaggtcagct | cggcccaccc | tctgccctgg | gagtgaccgc | 1680 |
| tgtgccaacc | tctgtcccta | cagggcagcc | ccgagagcca | caggtgtaca | ccctgccccc | 1740 |
| atcccaggag | gagatgacca | agaaccaggt | cagcctgacc | tgcctggtca | aaggcttcta | 1800 |
| ccccagcgac | atcgccgtgg | agtgggagag | caatgggcag | ccggagaaca | actacaagac | 1860 |

```
cacgcctccc gtgctggact ccgacggctc cttcttcctc tacagcaggc taaccgtgga    1920
caagagcagg tggcaggagg ggaatgtctt ctcatgctcc gtgatgcatg aggctctgca    1980
caaccactac acacagaaga gcctctccct gtctctgggt aaatgagtgc cagggccggc    2040
aagcccccgc tccccgggct ctcggggtcg cgcgaggatg cttggcacgt accccgtcta    2100
catacttccc aggcacccag catggaaata agcacccac cactgccctg ctcgaattc     2160
```

```
<210> SEQ ID NO 32
<211> LENGTH: 94
<212> TYPE: DNA
<213> ORGANISM: Artificial Sequence
<220> FEATURE:
<221> NAME/KEY: CDS
<223> OTHER INFORMATION: 544gH1 T1

<400> SEQUENCE: 32
agtgtgaggt gcaattggtc cagtcaggag cagaggttaa gaagcctggt gcttccgtca    60
aagtttcgtg taaggctagc ggctacaggt tcac                                94

<210> SEQ ID NO 33
<211> LENGTH: 96
<212> TYPE: DNA
<213> ORGANISM: Artificial Sequence
<220> FEATURE:
<221> NAME/KEY: CDS
<223> OTHER INFORMATION: 544gH1 T2

<400> SEQUENCE: 33
gtggcattaa tcccgggaat cagtacacta catataaaag aaatctaaag ggcagagcaa    60
cgctgaccgc ggacacctcc acaagcactg tctaca                              96

<210> SEQ ID NO 34
<211> LENGTH: 95
<212> TYPE: DNA
<213> ORGANISM: Artificial Sequence
<220> FEATURE:
<221> NAME/KEY: CDS
<223> OTHER INFORMATION: 544gH1 T3

<400> SEQUENCE: 34
agagaaggct acggtaatta cggagcctgg ttcgcctact ggggccaggg taccctagtc    60
acagtctcct cagcttctac aaagggccca agaaa                               95

<210> SEQ ID NO 35
<211> LENGTH: 94
<212> TYPE: DNA
<213> ORGANISM: Artificial Sequence
<220> FEATURE:
<221> NAME/KEY: CDS
<223> OTHER INFORMATION: 544 gH1 B1

<400> SEQUENCE: 35
ggaccaattg cacctcacac tgcactccct tgagaatgag tgccaggaac acgagagaga    60
atccgaagtc catggtggcg gcaagctttt attc                                94

<210> SEQ ID NO 36
<211> LENGTH: 97
<212> TYPE: DNA
<213> ORGANISM: Artificial Sequence
<220> FEATURE:
<221> NAME/KEY: CDS
<223> OTHER INFORMATION: 544gH1 B2
```

<400> SEQUENCE: 36
gattcccggg attaatgcca ccgatccatt ccaggccttg tcccggagcc tgcctgaccc    60
aatgaatcca ataatttgtg aacctgtagc cgctagc    97

<210> SEQ ID NO 37
<211> LENGTH: 93
<212> TYPE: DNA
<213> ORGANISM: Artificial Sequence
<220> FEATURE:
<221> NAME/KEY: CDS
<223> OTHER INFORMATION: 544gH1 B3

<400> SEQUENCE: 37
cgtaattacc gtagccttct ctagtacaat agtacactgc ggtgtcctcg gatctcagag    60
atgacagctc catgtagaca gtgcttgtgg agg    93

<210> SEQ ID NO 38
<211> LENGTH: 21
<212> TYPE: DNA
<213> ORGANISM: Artificial Sequence
<220> FEATURE:
<221> NAME/KEY: CDS
<223> OTHER INFORMATION: 544gH1 F1

<400> SEQUENCE: 38
gaataaaagc ttgccgccac c    21

<210> SEQ ID NO 39
<211> LENGTH: 22
<212> TYPE: DNA
<213> ORGANISM: Artificial Sequence
<220> FEATURE:
<221> NAME/KEY: CDS
<223> OTHER INFORMATION: 544gH1 R1

<400> SEQUENCE: 39
tttcttgggc cctttgtaga ag    22

<210> SEQ ID NO 40
<211> LENGTH: 87
<212> TYPE: DNA
<213> ORGANISM: Artificial Sequence
<220> FEATURE:
<221> NAME/KEY: CDS
<223> OTHER INFORMATION: 544 gL1 T1

<400> SEQUENCE: 40
gcttcccggg gtgacgttca agtgacccag agcccatcca gcctgagcgc atctgtagga    60
gaccgggtca ccatcacttg tagatcc    87

<210> SEQ ID NO 41
<211> LENGTH: 90
<212> TYPE: DNA
<213> ORGANISM: Artificial Sequence
<220> FEATURE:
<221> NAME/KEY: CDS
<223> OTHER INFORMATION: 544 gL1 T2

<400> SEQUENCE: 41
tatctgcaca aaccaggtaa agccccacaa ttgctcatct acggaatctc taacagattt    60
agtggtgtac cagacaggtt cagcggttcc    90

<210> SEQ ID NO 42

```
<211> LENGTH: 91
<212> TYPE: DNA
<213> ORGANISM: Artificial Sequence
<220> FEATURE:
<221> NAME/KEY: CDS
<223> OTHER INFORMATION: 544gL1 T3

<400> SEQUENCE: 42
agatttcgcc acttattact gtttacaagg tacacatcag ccgtacacat tcggtcaggg      60
tactaaagta gaaatcaaac gtacggcgtg c                                    91

<210> SEQ ID NO 43
<211> LENGTH: 88
<212> TYPE: DNA
<213> ORGANISM: ARTIFICIAL SEQUENCE
<220> FEATURE:
<221> NAME/KEY: CDS
<223> OTHER INFORMATION: 544gL1 B1

<400> SEQUENCE: 43
gaacgtcacc ccgggaagca ggaatccaga acaacagaag caccaacagc ctaacaggca      60
acttcatggt ggcggcttcg aatcatcc                                        88

<210> SEQ ID NO 44
<211> LENGTH: 88
<212> TYPE: DNA
<213> ORGANISM: Artificial Sequence
<220> FEATURE:
<221> NAME/KEY: CDS
<223> OTHER INFORMATION: 544gL1 B2

<400> SEQUENCE: 44
ctttacctgg tttgtgcaga taccaagaca aaaaggtgtt cccataactg tttgcaagac      60
tctgactgga tctacaagtg atggtgac                                        88

<210> SEQ ID NO 45
<211> LENGTH: 90
<212> TYPE: DNA
<213> ORGANISM: Artificial Sequence
<220> FEATURE:
<221> NAME/KEY: CDS
<223> OTHER INFORMATION: 544gL1 B3

<400> SEQUENCE: 45
aacagtaata agtggcgaaa tcttctggct ggagagacga gatcgtgagg gtgaaatcag      60
taccacttcc ggaaccgctg aacctgtctg                                      90

<210> SEQ ID NO 46
<211> LENGTH: 20
<212> TYPE: DNA
<213> ORGANISM: Artificial Sequence
<220> FEATURE:
<221> NAME/KEY: CDS
<223> OTHER INFORMATION: 544gL1 F1

<400> SEQUENCE: 46
ggatgattcg aagccgccac                                             20

<210> SEQ ID NO 47
<211> LENGTH: 21
<212> TYPE: DNA
<213> ORGANISM: ARTIFICIAL SEQUENCE
<220> FEATURE:
<221> NAME/KEY: CDS
<223> OTHER INFORMATION: 544gL1 R1
```

<400> SEQUENCE: 47
gcacgccgta cgtttgattt c                                            21

<210> SEQ ID NO 48
<211> LENGTH: 339
<212> TYPE: DNA
<213> ORGANISM: mouse
<220> FEATURE:
<221> NAME/KEY: CDS
<223> OTHER INFORMATION: DNA sequence of mouse monoclonal 5/44 VL

<400> SEQUENCE: 48
gatgttgtgg tgactcaaac tccactctcc ctgcctgtca gctttggaga tcaagtttct    60
atctcttgca ggtctagtca gagtcttgca aacagttatg ggaacacctt tttgtcttgg   120
tacctgcaca agcctggcca gtctccacag ctcctcatct atgggatttc aacagattt   180 tctggggtgc cagacaggtt cactggcagt ggttcaggga cagatttcac actcaagatc   240
agcacaataa agcctgagga cttgggaatg tattactgct acaaggtac acatcagccg   300 tacacgttcg gaggggggac caagctggaa ataaaacgt                          339

<210> SEQ ID NO 49
<211> LENGTH: 363
<212> TYPE: DNA
<213> ORGANISM: mouse
<220> FEATURE:
<221> NAME/KEY: CDS
<223> OTHER INFORMATION: DNA sequence of mouse monoclonal 5/44 VH

<400> SEQUENCE: 49
gaggtccaac tgcagcagtc tgggactgta ctggcaaggc ctggggcttc cgtgaagatg    60
tcctgcaagg cttctggcta caggtttacc aactactgga ttcactgggt aaaacagagg   120
cctgggcagg gtctagaatg gattggtggt attaatcctg gaaataatta tactacgtat   180
aagaggaact tgaagggcaa ggccacactg actgcagtca catccgccag cactgcctac   240
atggacctca gcagcctgac aagtgaggac tctgcggtct attactgtac aagagagggc   300
tatggtaact acggggcctg gtttgcttac tggggccagg ggactctggt caccgtctcc   360
tca                                                                 363

<210> SEQ ID NO 50
<211> LENGTH: 9
<212> TYPE: DNA
<213> ORGANISM: Artificial Sequence
<220> FEATURE:
<221> NAME/KEY: PRIMER
<223> OTHER INFORMATION: sequence within oligonucleotide primer

<400> SEQUENCE: 50 gccgccacc                                                             9

<210> SEQ ID NO 51
<211> LENGTH: 101
<212> TYPE: DNA
<213> ORGANISM: Artificial Sequence
<220> FEATURE:
<221> NAME/KEY: PRIMER
<223> OTHER INFORMATION: 5' oligonucleotide primer -continued

```
<400> SEQUENCE: 51
gcgcgcaagc ttgccgccac catggacttc ggattctctc tcgtgttcct ggcactcatt      60
ctcaagggag tgcagtgtga ggtgcagctc gtcgagtctg g                        101
```